United States Patent
Becker

(10) Patent No.: US 9,157,430 B2
(45) Date of Patent: Oct. 13, 2015

(54) PUMP MODULE, PUMP MODULE AND PUMP SYSTEM

(75) Inventor: Michael Becker, Knittlingen (DE)

(73) Assignee: FRESENIUS KABI DEUTSCHLAND GMBH, Bad Homburg (DE)

( * ) Notice: Subject to any disclaimer, the term of this patent is extended or adjusted under 35 U.S.C. 154(b) by 732 days.

(21) Appl. No.: 13/272,244

(22) Filed: Oct. 13, 2011

(65) Prior Publication Data

US 2012/0207635 A1    Aug. 16, 2012

Related U.S. Application Data

(60) Provisional application No. 61/392,495, filed on Oct. 13, 2010, provisional application No. 61/392,490, filed on Oct. 13, 2010, provisional application No. 61/392,492, filed on Oct. 13, 2010, provisional application No. 61/392,494, filed on Oct. 13, 2010.

(30) Foreign Application Priority Data

| Oct. 13, 2010 | (EP) | ................................ 10187377 |
| Oct. 13, 2010 | (EP) | ................................ 10187378 |
| Oct. 13, 2010 | (EP) | ................................ 10187380 |
| Oct. 13, 2010 | (EP) | ................................ 10187381 |

(51) Int. Cl.

| F01C 5/00 | (2006.01) |
| F03C 2/00 | (2006.01) |
| F03C 4/00 | (2006.01) |
| F04C 2/00 | (2006.01) |
| F04C 5/00 | (2006.01) |
| F04B 43/12 | (2006.01) |

(Continued)

(52) U.S. Cl.
CPC .............. *F04B 43/12* (2013.01); *A61M 5/1413* (2013.01); *A61M 5/14232* (2013.01); *F01C 9/005* (2013.01); *F04B 43/082* (2013.01); *F04B 43/123* (2013.01); *F04B 43/1207* (2013.01); *F04B 43/1238* (2013.01); *F04B 43/1253* (2013.01); *F04B 43/14* (2013.01); *F04C 9/005* (2013.01); *A61M 39/24* (2013.01); *A61M 39/26* (2013.01); *A61M 2005/16868* (2013.01); *A61M 2005/16872* (2013.01); *A61M 2205/128* (2013.01); *A61M 2205/3351* (2013.01); *A61M 2205/3355* (2013.01); *A61M 2205/6045* (2013.01)

(58) Field of Classification Search
USPC ........................ 418/45, 49–50; 417/474, 476
See application file for complete search history.

(56) References Cited

U.S. PATENT DOCUMENTS

| 3,922,119 A | 11/1975 | Rosenquist |
| 4,351,797 A | 9/1982 | Bellhouse et al. |

(Continued)

FOREIGN PATENT DOCUMENTS

| DE | 1078447 | 3/1960 |
| DE | 1528971 | 7/1969 |

(Continued)

*Primary Examiner* — Theresa Trieu
(74) *Attorney, Agent, or Firm* — Occhiuti & Rohlicek LLP

(57) ABSTRACT

The invention concerns a wobble pump base module and a wobble pump system. The invention-based wobble pump base module (40) comprises a wobble pump drive system (43), a wobble device (41), a receptacle (42) for a pump module (1) and a pretensioning device (56), wherein the pretensioning device (56) flexibly pretensions the pump module (1) housed in the receptacle (42) against the wobble device (41).

18 Claims, 21 Drawing Sheets

Figure 1:
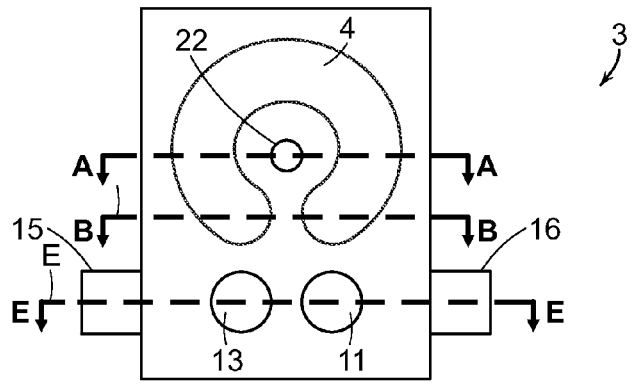

(51) Int. Cl.
*F04B 43/08* (2006.01)
*F04C 9/00* (2006.01)
*F01C 9/00* (2006.01)
*A61M 5/14* (2006.01)
*A61M 5/142* (2006.01)
*F04B 43/14* (2006.01)
*A61M 39/24* (2006.01)
*A61M 39/26* (2006.01)
*A61M 5/168* (2006.01)

(56) References Cited

U.S. PATENT DOCUMENTS

| | | | |
|---|---|---|---|
| 4,392,794 A | | 7/1983 | Foxcroft |
| 4,483,666 A | * | 11/1984 | Schubert et al. ................ 418/45 |
| 4,544,329 A | | 10/1985 | O'Boyle |
| 5,281,111 A | | 1/1994 | Plambeck et al. |
| 5,458,469 A | | 10/1995 | Hauser |
| 5,466,133 A | | 11/1995 | Tuck |
| 5,533,886 A | | 7/1996 | Von Der Heyde et al. |
| 5,720,721 A | | 2/1998 | Dumas et al. |
| 6,293,926 B1 | | 9/2001 | Sorensen et al. |
| 6,296,460 B1 | | 10/2001 | Smith |
| 6,595,950 B1 | | 7/2003 | Miles et al. |
| 7,393,189 B2 | | 7/2008 | Davis et al. |
| 2009/0221964 A1 | | 9/2009 | Rotem et al. |
| 2010/0057058 A1 | | 3/2010 | Ziegler et al. |
| 2010/0243087 A1 | | 9/2010 | Morrissey |

FOREIGN PATENT DOCUMENTS

| | | |
|---|---|---|
| DE | 3227051 | 2/1984 |
| EP | 0604740 | 7/1994 |
| FR | 2079955 | 11/1971 |
| FR | 2690621 | 11/1993 |
| GB | 1495797 | 12/1977 |
| NL | 7509443 | 3/1976 |
| WO | 2010/088143 | 8/2010 |

\* cited by examiner

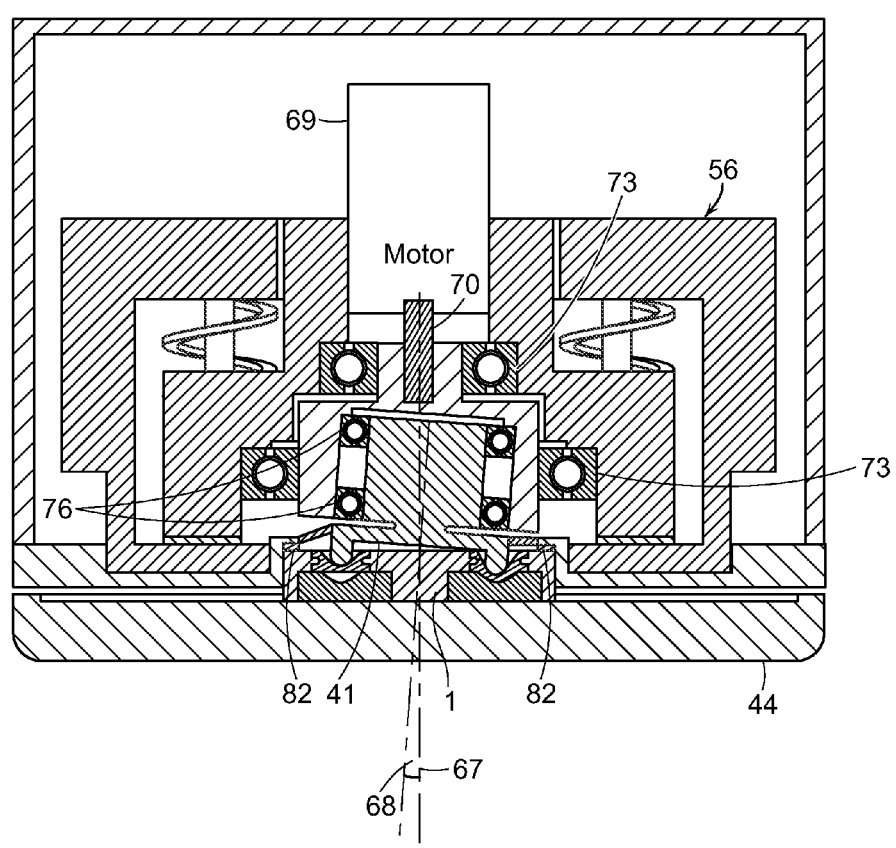

PUMP MODULE, PUMP MODULE AND PUMP SYSTEM

RELATED APPLICATIONS

Under 35 USC 119, this application claims the benefit of the priority date of U.S. Provisional application 61/392,495, 61/392,492, 61/392,490, and 61/392,494, and European applications 10187381.8, 10187377.6, 10187378.4, and 10187380.0, all of which were filed on Oct. 13, 2010. The contents of the foregoing applications are incorporated herein by reference.

TECHNICAL FIELD

The invention concerns a pump base module and a pump system, which comprises a pump module and a pump base module, in particular the invention concerns a wobble pump base module and a wobble pump system.

PRIOR ART

The U.S. Pat. No. 5,466,133 discloses a wobble pump. The wobble pump comprises a pump drive system and a wobble plate. Furthermore, the wobble pump comprises a membrane and a lower housing part, which together form a pump channel. The pump channel is formed by a circular recess in said housing part, wherein the circle is not closed. At one end of the circular recess a pump channel inlet is located, at the other end there is a pump channel outlet. Via screw joints, the lower housing part is firmly connected to a central housing part. The wobble device is located in the central housing part. The membrane is clamped between the lower housing part and the central housing part. Furthermore, the membrane is firmly connected to the wobble device. By means of the wobble pump drive system, the wobble device can be caused to swing, and the oscillation is transmitted to the membrane because of the firm connection with the membrane. The oscillation of the membrane corresponds to a peristaltic motion. Through a deformation of the membrane in a section between pump inlet and pump outlet, the pump channel is closed, and the closed section runs along with the oscillation from pump inlet to pump outlet. In this way, it is possible to transport a fluid through the pump channel. Back-pressure valves behind the pump channel inlet and the pump channel outlet prevent an undesired backflow.

The DE 32 27 051 A1 discloses a flexible-tube pump for medical applications. The flexible-tube pump is designed as a wobble pump. The flexible-tube pump comprises a pump drive system and a wobble plate, which can be caused to swing by means of the pump drive system. The flexible-tube pump has a hinged cover in which a tube can be inserted. By means of the swinging wobble plate, the inserted tube is compressed at a place in the circular pump section that moves along with the oscillation so that a fluid can be transported through the tube. The contusion point is long enough that in a phase of oscillation an inlet section and an outlet section of the tube can be compressed at the same time so that the tube is always closed at least one place. In this way, an undesired flow of the fluid is prevented.

BRIEF DESCRIPTION OF THE INVENTION

The invention-based wobble pump base module comprises a wobble pump drive system, an oscillation device, a receptacle for a pump module and a pretensioning device, wherein the pretensioning device resiliently pretensions the pump module received in the receptacle against the wobble device.

Because of the fact that the pump module resiliently pretensions the wobble device, it can be guaranteed that the pump module and the wobble device received in the receptacle assume a defined position in relation to one another. This is especially advantageous in the event that the pump module is designed as a disposable item ("disposable"), which means that it is removed after a single use and replaced with a new pump module. The defined positions of wobble device and pump module prevent that the pump properties change to an undesired extent when the pump module is exchanged. Since the pump module is inserted or can be inserted in a wobble pump or a wobble pump base module (see the following description), the pump module can also be described as a pump module cassette.

The invention-based wobble pump system comprises an invention-based wobble pump base module and a pump module, wherein the pump module comprises a base and a flexibly deformable membrane, wherein base and membrane form a line-shaped pump channel that is curved at least in sections in such a way that through a wobble deformation of the membrane a fluid can be pumped through the pump channel, wherein the pump module is received in the receptacle of the wobble pump base module in such a way that by means of the pretensioning device the pump module and the wobble device are resiliently pressed against one another.

A further invention-based pump module comprises a base and a flexibly deformable membrane, wherein base and membrane form a line-shaped pump channel that is curved at least in sections, and the base comprises a pump channel inlet and a pump channel outlet, wherein the pump channel inlet and the pump channel outlet are connected with the pump channel for supplying a fluid into the pump channel and discharging a fluid from the pump channel, so that through a wobbling deformation of the membrane a fluid can be pumped through the pump channel from the pump channel inlet to the pump outlet.

The invention-based pump module can be produced in an inexpensive and robust manner. By designing the pump channel from a membrane and a base, it is possible to produce a pump channel with defined and reproducible measurements, allowing a plurality of pump modules to achieve high accuracy in the production rate. Because of the fact that the pump module can be produced in an inexpensive and reproducible manner, the invention-based pump module qualifies as a disposable item ('disposable") intended merely for single use.

In particular, the pump module can be used as a component of a wobble pump. Basically, an invention-based pump module can be used also for other pump types.

A further invention-based wobble pump base module comprises a wobble pump drive system having an oscillation device and a receptacle, wherein the receptacle is designed in such a way that the pump module can be manually applied or inserted in the receptacle, and the pump module can be manually removed from the receptacle.

The invention-based wobble pump base module allows for a manual insertion of a pump module, without using additional tools, thus producing a functioning wobble pump. It is just as simple to remove the pump module from the wobble pump base module. Because of these facts, the wobble pump base module is especially well suited for the use of pump modules which are designed as a disposable item ("disposable") and are replaced after each use.

According to an advantageous development, the wobble device of the wobble pump base module is mounted in axially movable fashion along its rotational axis. The axial bearing of the wobble device makes it possible that the wobble device can be moved in relation to the pump base module to exert a defined contact pressure on the membrane of the pump module.

According to a further advantageous development, the wobble device comprises pressure measuring devices which allow the pressure inside the pump channel to be measured through the membrane of the pump base module. By measuring the pressure in the pump channel, it is possible, depending on the motion state of the wobble device, to measure to pressure when the pump channel inlet and the pump channel outlet are closed and when the pump channel inlet and the pump channel outlet are opened.

A further invention-based wobble pump system comprises an invention-based pump module and an invention-based wobble pump base module, wherein the pump module is received in the receptacle of the wobble pump base module.

A further invention-based pump module for a wobble pump comprises a line-shaped pump channel that is curved at least in sections, a pump channel inlet and a pump channel outlet, wherein the pump channel inlet and the pump channel outlet are connected with the pump channel for supplying a fluid into the pump channel and discharging a fluid from the pump channel, so that through a periodically rotating deformation of the pump channel a fluid can be pumped through the pump channel from the pump channel inlet to the pump outlet, wherein the pump channel in the section between the pump channel inlet and the pump channel outlet is designed in a way that differs from a genuine circular design.

In the context of the invention, a "circular design" refers to a circular arc, which can be open or closed (when closed it forms a circle). Another pump channel has circular sections which are, however, designed with different radii in relation to a mutual center. In the context of the invention, said pump channel is considered also as having a design that differs from a circular arc.

For example, when the pump channel has a design that differs from a genuine circular design, it is possible within the oscillation of a wobble device to securely close the pump channel inlet and the pump channel outlet simultaneously. As a result, a situation can be prevented in which the pump channel is opened between pump outlet and pump inlet and an undesired discharge of the fluid occurs. In case of a wobble device having an axially movable design and/or a wobble device having an at least partially rebounding design, it is possible alternatively or additionally to optimize during its periodically rotating oscillation the axial movement of amplitude of the wobble device or parts of the wobble device. This is possible especially during transition phases in which the wobble device has to bridge the pump channel free section between the pump channel inlet and the pump channel outlet.

Furthermore, it is possible alternatively or additionally to achieve by means of a formation of overlapping pump channel sections a compression and thus an increase of pressure of a fluid being transported through the pump channel. Alternatively or additionally, when the design of the pump channel differs from a genuine circular design, for example when the pump channel is divided in at least a first and a second area, it is possible to provide a section of the pump channel for measuring purposes or for the purpose of pressure compensation.

A further invention-based wobble pump base module comprises a wobble pump drive system with an wobble device, wherein the wobble device comprises a line-shaped bar which is curved at least in sections and which is able to swing for deforming in a wobble manner a tube or a membrane, wherein the design of the bar differs from a genuine circular design.

Because of the fact that the bar of the wobble device has a design that differs from a genuine circular design, it is possible within the oscillation of a wobble device to securely close the pump channel inlet and the pump channel outlet simultaneously. As a result, a situation can be prevented in which the pump channel is opened for only a moment between pump outlet and pump inlet and an undesired discharge of the fluid occurs. Alternatively or additionally, when the bar has a design that differs from a circular design, it is possible in conjunction with a respectively designed section of the pump channel to generate in the context of the oscillation a pressure increase within an area of the pump channel.

Alternatively, instead of designing the wobble device with a bar, the membrane can be designed with a respective bulge. The embodiment comprising the bulge, which can also be depicted as a projection, proves to be advantageous because in this way an evenly distributed press force can be exerted on the membrane. Furthermore, the wobble pump is quite sensitive toward a pressure variation at the pump channel inlet and/or outlet. Moreover, it is uncritical with regard to lateral tolerances of the wobble device toward the membrane, which is especially important for the "disposable" feature. In this case, the wobble device can have a planar surface which interacts with the bulge of the membrane. It is preferred that during circulation of the wobble device a permanent or largely permanent contact exists between the membrane and the wobble device. In particular, the membrane is permanently or largely permanently pretensioned. As a result, the pump performance is insensitive toward a variation of the initial pressure which is, for example, affected by the level of the bag. In a preferred embodiment of the invention, the wobble device and the membrane are not connected, for example, by being screwed together. They adjoin each other.

A further invention-based wobble pump system comprises an invention-based pump module and an invention-based wobble pump base module, wherein the bar of the wobble device of the wobble pump base module is designed at least in sections in accordance with the section of the pump channel between pump channel inlet and pump channel outlet.

The bar of the wobble device and the pump channel correspond at least in sections to a form that differs from a genuine circular design. The bar can be continued in one or both directions so that the part of the bar corresponding with the pump channel forms only a section of the bar.

A further invention-based pump module for a medical pump, in particular for a wobble pump, comprises a pump channel and a valve unit (or chamber) connected with the pump channel, wherein a fluid can be pumped through the pump channel and the valve unit, wherein a first wall section of the valve unit is flexible, and the pump module has a flexible valve body which is arranged in the valve unit, wherein the valve body can occupy an idle position in which the valve body closes the valve unit to prevent fluid from passing through, and wherein the valve body can occupy an operation position in which the valve body allows the fluid to flow through the valve unit and in which the valve body can be operated by means of a deformation of the first wall section of the valve bodies so that the fluid can flow through the valve unit.

By means of the valve body, it is possible to prevent fluid from flowing involuntarily through the pump module. Preferably, the valve formed in this way is used as "anti-free-flow-valve", i.e., a valve that is closed in its basic position and in this way prevents fluid from flowing involuntarily through the pump module. In particular, this involves the situation when the pump channel is still open, for example, because the pump module has not yet been inserted in a respective pump base module. Only when the valve has been actively opened, the flow through the pump module is released. The opening of the valve takes place by means of a deformation of the first wall section. For example, by means of the deformation of the wall section, the valve body is pressed into a confirmation position or, alternatively, a space is opened that can be occupied by the valve body. Because of the fact that the valve body is activated by means of a flexible wall section, the means for said activation, for example, a hand or a mechanical device, do not come in direct contact with the fluid to be transported by the pump module. Moreover, a pump module having such a valve can be produced in an inexpensive manner. As a result, the pump module is especially well suited to be uses as a disposable item ("disposable").

It is especially preferred that the pump module is designed as module for a wobble pump, comprising a base and a membrane which form a pump channel. The base can form at least a section of the valve unit. In this way, it is possible to produce with only a few parts a pump module which is inexpensive and robust and which is sufficiently accurate, especially when used for medical applications.

A further invention-based pump base module comprises a pump drive system, a receptacle and a valve actuator, wherein the receptacle is designed in such a way that the pump module can be applied or inserted in the receptacle and that the pump module can be removed from the receptacle, wherein the valve actuator is designed in such a way that it deforms the first flexible wall section of the valve unit of the pump module when the pump module is applied or inserted or after the pump module is applied or inserted, thus bringing the valve body in operation position.

The invention-based pump base module brings the valve body in operation position, i.e., it opens the valve of the pump module. In this way, it can be guaranteed that the valve is opened only when it is intended to be opened, for example, when the pump module has been correctly inserted or possibly when the pump base module has accepted a respective position, for example, after initiating an initialization or pump program.

A further invention-based pump system comprises an invention-based pump module and an invention-based pump base module.

Further preferred embodiments of the invention are described in the dependent claims.

The pump modules, pump base modules, in particular wobble pump base modules, pump systems, in particular wobble pump systems described here are well suited for an application in the medical field. Preferred applications of these devices involve a use as enteral pumps, for example, for pumping nutrition solutions or for use as infusion pumps for intravenously infusing medications. Further applications involve epidural infusions, intramuscular or subcutaneous infusions.

Subsequently, the invention is described in more detail by means of different embodiments. The embodiments are depicted by several figures.

BRIEF DESCRIPTION OF THE FIGURES IN THE DRAWINGS

Figure 34:
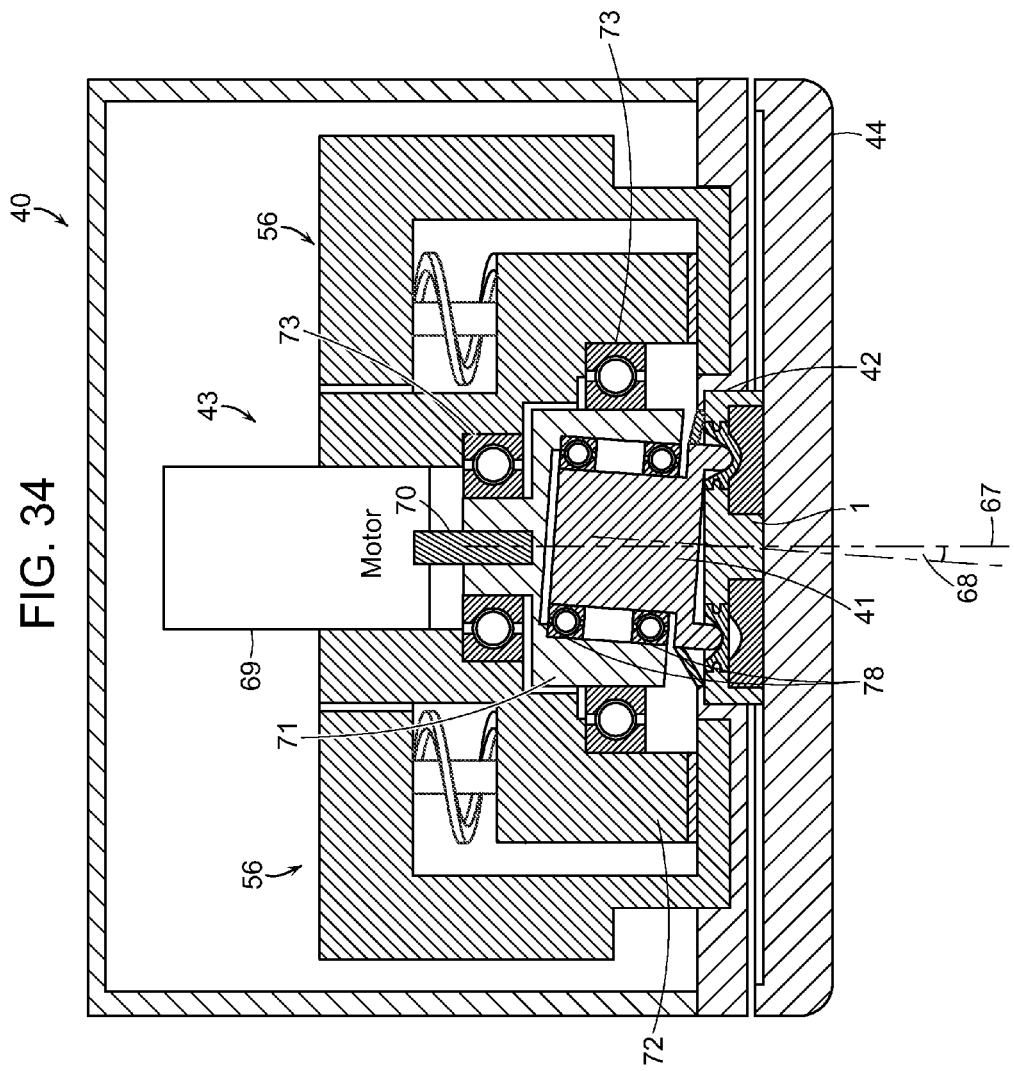
Figure 35:
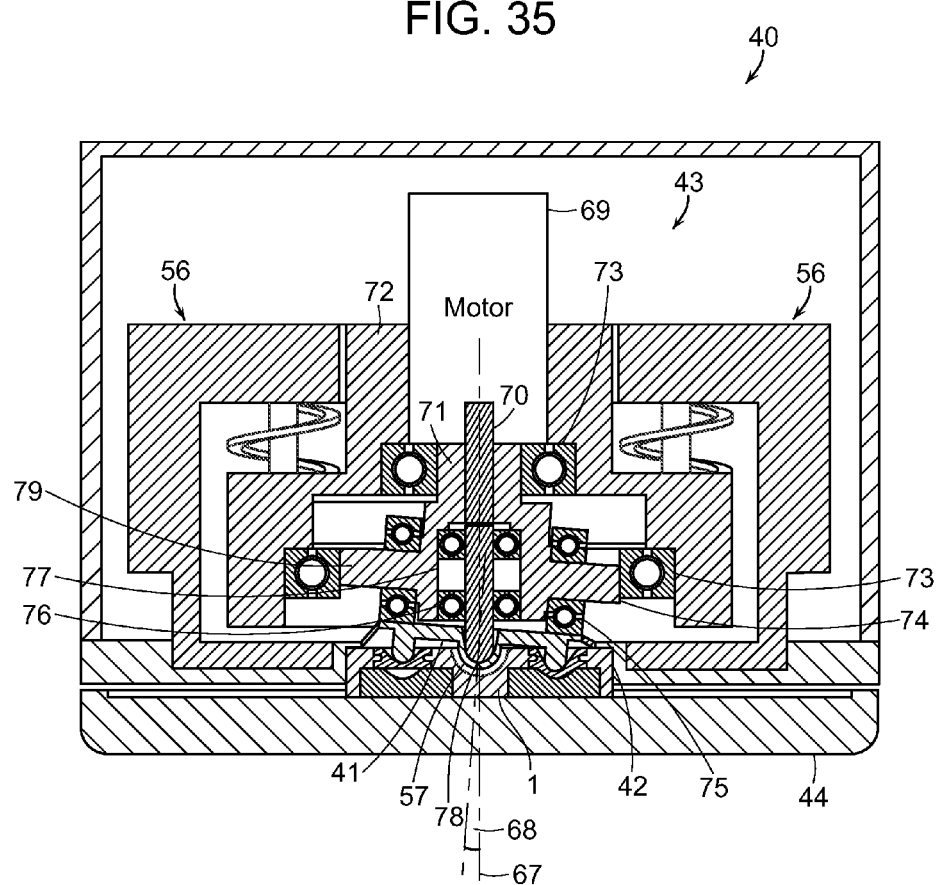
Figure 36:
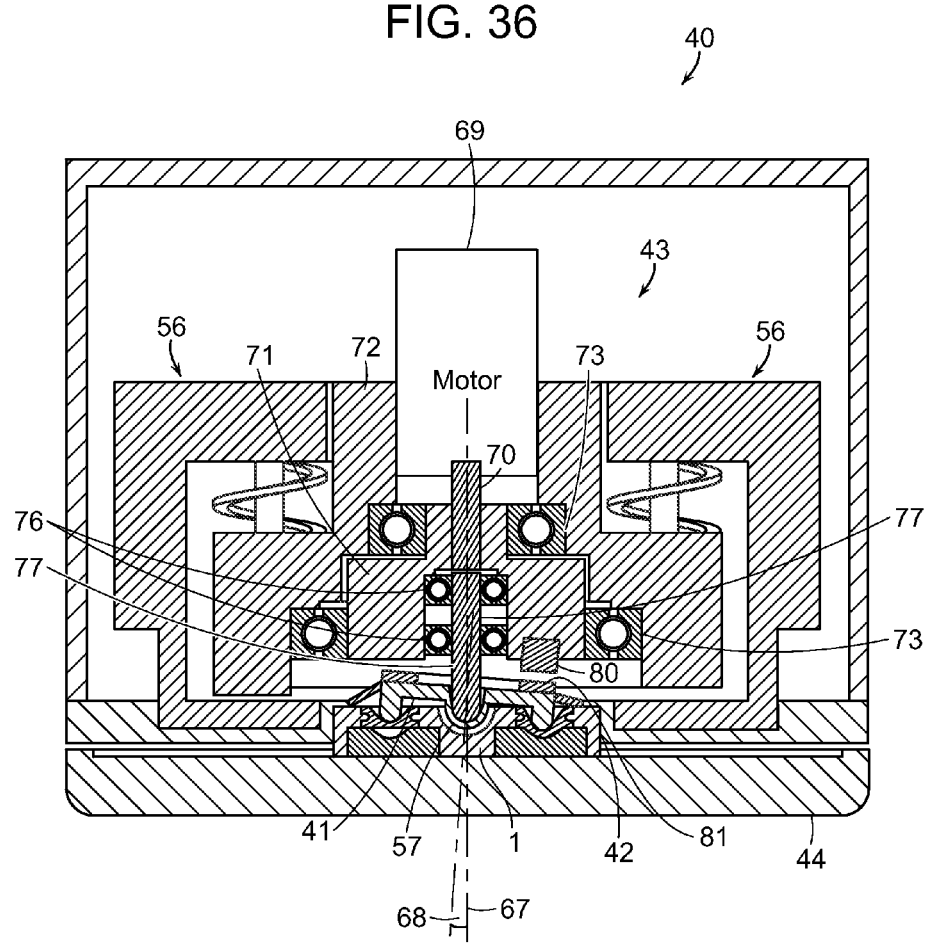

The figures show:
FIG. 1 a top view of a cover and membrane of a first embodiment of the pump module,
FIG. 2 a top view of a base of the first embodiment of the pump module,
FIG. 3 a perspective view of a wobble device,
FIG. 4 a cross-section through the wobble device and the pump module according to the first embodiment along a cutting line A-A, see FIG. 1,
FIG. 5 a cut through the wobble device and the pump module according to the first embodiment along a cutting line B-B, see FIG. 1, wherein the pump channel outlet and the pump channel inlet of the wobble device are closed,
FIG. 6 a cut through a second embodiment of a pump module, wherein the elements of the pump module are shown in an exploded view,
FIG. 7 the second embodiment of the pump module in assembled state,
FIG. 8 a top view of a cover and membrane of a third embodiment of a pump module,
FIG. 9 a perspective view of a second embodiment of a wobble device,
FIG. 10 a cut through the third embodiment of the pump module and the wobble device along the cutting line A-A depicted in FIG. 8,
FIG. 11 a top view of the base of a fourth embodiment of a pump module,
FIG. 12 a cut through a fourth embodiment of the pump module along the cutting line B-B depicted in FIG. 11
FIG. 13 a cut through a fourth embodiment of the pump module and the wobble device along the cutting line A-A depicted in FIG. 11,
FIG. 14 a top view of the base of a fifth embodiment of a pump module,
FIG. 15 a top view of a cover and membrane of the fifth embodiment of a pump module,
FIG. 16 a top view of a cover and membrane of a sixth embodiment of a pump module,
FIG. 17 a top view of a cover of the sixth embodiment of a pump module,
FIG. 18 a bottom view of a wobble device according to a third embodiment,
FIG. 19 a lateral view of the wobble device shown in FIG. 18,
FIG. 20 a lateral view of a model of the wobble device shown in FIG. 18,
FIG. 21 a top view of a seventh embodiment of a pump module,
FIG. 22 a cut along the cutting line A-A through the pump module shown in FIG. 21 with partially compressed pump channel,
FIG. 23 a cut along the cutting line D-D through the pump module shown in FIG. 21,
FIG. 24 a cut along the cutting line E-E through the pump module according to the first embodiment, see FIG. 1, wherein a valve body of the pump module occupies an idle position,
FIG. 25 a cut along the cutting line E-E through the pump module according to the first embodiment, see FIG. 1, wherein a valve body of the pump module occupies an operation position,
FIG. 26 a cut along the cutting line E-E through an eighth embodiment of a pump module, see FIG. 1, wherein a valve body of the pump module occupies an idle position,
FIG. 27 a cut along the cutting line E-E through an eighth embodiment of a pump module, see FIG. 1, wherein a valve body of the pump module occupies an operation position,
FIG. 28 a variation of the cover shown in FIG. 8 in which cover the bulge of the membrane is interrupted in one section,
FIG. 29 a cut along the cutting line F-F through a pump module with the cover shown in FIG. 28 and a wobble device,
FIG. 30 a top view of a wobble pump base module with an opened cover and a receptacle for a pump module, FIG. 31 a top view of the wobble pump base module shown in FIG. 30, in which wobble pump base module the pump module has been received in the receptacle, FIG. 32 a cut through the wobble pump base module in which a pump module has been received in the receptacle when the cover is closed, FIG. 33 a cut through the wobble pump base module in which a pump module has been received in the receptacle when the cover is closed, and with a first wobble drive system and a first wobble device, FIG. 34 a cut through the wobble pump base module in which a pump module has been received in the receptacle when the cover is closed, and with a second wobble drive system and a second wobble device, FIG. 35 a cut through the wobble pump base module in which a pump module has been received in the receptacle when the cover is closed, and with a third wobble drive system and a third wobble device, FIG. 36 a cut through the wobble pump base module in which a pump module has been received in the receptacle when the cover is closed, and with a fourth wobble drive system and a fourth wobble device, and FIG. 37 a cut through the wobble pump base module in which a pump module has been received in the receptacle when the cover is closed, and with a second wobble drive system and a second wobble device, FIG. 38.a to 38.c an embodiment of the pump module in non-assembled state and in assembled state, FIGS. 39.a and 39.b a wobble plate with a ramp, and FIGS. 40.a and 40.b calculations regarding pump performance with and without ramp.

DESCRIPTION OF THE DIFFERENT TYPES OF EMBODIMENT

In the figures similar and corresponding components are provided with the same reference numerals.

FIGS. 1, 2, 4 and 5 show a first embodiment of a pump module 1 or individual elements of the pump module 1. As shown, for example, in FIG. 33, the pump module 1 is designed to be used with a wobble pump base module. This does not exclude the pump module 1 from being used with other types of pumps, although it is preferred to use it in the manner mentioned above. Pump module and wobble pump base module form a wobble pump system by means of which fluid, i.e., a gas or any other fluid, can be transported.

The pump module comprises a base 2, a cover 3 and a flexibly deformable membrane 4. The base 2 and the membrane 4 form a line-shaped pump channel 5 that is curved at least in sections. The base 2 comprises a pump channel inlet 6 and a pump channel outlet 7. The pump channel inlet 6 and the pump channel outlet 7 are connected with the pump channel 5 for supplying a fluid into the pump channel 5 and discharging a fluid from the pump channel 5. The wobble deformation of the membrane 4 results in a circular local compression of the pump channel 5, making it possible that a fluid can be pumped through the pump channel 5 from the pump channel inlet 6 to the pump channel outlet 7.

Basically, it is also possible to pump a fluid from the pump channel outlet 7 to the pump channel inlet 6 by reversing the oscillation movement.

In this embodiment, the base 2 comprises a groove 23. The pump channel 5 is formed by the groove 23 and the in uncompressed condition planar lower surface of the (in this embodiment) flat and on both sides planar membrane 4. The groove 23 has a slightly curved profile, so that the membrane 4 can be pressed through a wobble device, for example, through the wobble plate 41 shown in FIG. 3, to seal the surface of the groove 23. During the process, the membrane is not exposed to excessive shearing forces. Alternatively, it is also possible to design the membrane 4 with a groove and to provide the base 2 with a planar surface, or to provide membrane 4 and base 2, respectively, with a design that differs from a planar surface to form the pump channel 5.

The pump channel 5 does not have a completely circular design but it is interrupted by a bar 26. The bar ensures that there is only one way for the fluid to flow between the pump channel inlet 6 and pump channel outlet 7.

Pump channel inlet 6 and pump channel outlet 7, respectively, directly adjoin one side of the bar 26. As a result, it is possible to use almost the complete volume of the pump channel 5 for transporting the fluid.

The pump channel inlet 6 and the pump channel outlet 7 are here designed as groove-shaped recesses (see FIG. 5), which are arranged at the bottom of the respective end of the pump channel 5. Alternatively, it is also possible to use different forms, for example, channels with round or elliptic openings. The groove-shaped recesses are positioned vertically to the pump channel 5 and end in a first cylindrical recess 24 or a second cylindrical recess 25. The first cylindrical recess is part of a valve unit 12, the second cylindrical recess is part of a pressure measuring chamber 10 (for example, see FIG. 16).

The membrane 4 is connected with the cover 3. It is possible to use different types of connections, for example, adhesively joined, especially by gluing or molding, wherein the molding process includes also injection-molding, or a force-fit connection with clamps. It is preferred that the membrane 4 is injection-molded to the cover 3, as has been done in this embodiment. To improve the adherence of the membrane 4 to the cover 3, the cover 3 comprises a projection 27 along the inside surface facing the pump channel 5 (see FIG. 5), which projection is encompassed on its upper and lower surface by the membrane 4.

Figure 6:
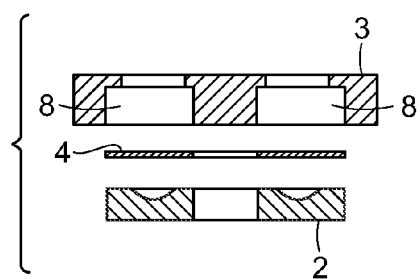
Figure 7:
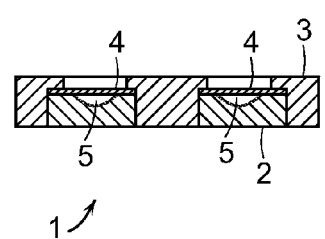

FIGS. 6 and 7 show an alternative embodiment of a pump module 1 in which the membrane 4 is attached by clamps. In this model, the membrane 4 forms a separate flat element with a planar upper and lower surface, which is clamped between base 2 and cover 3.

Alternatively, the membrane 4 can also be connected with the base 2, in particular in connection with the types of connection mentioned for the cover 3.

The base 2 and the cover 3 have an undercut-free design. As a result, the base 2 and the cover 3 can be produced without using costly tools in an inexpensive manner. In particular, it is not required to perform a costly process of demolding.

Figure 5:
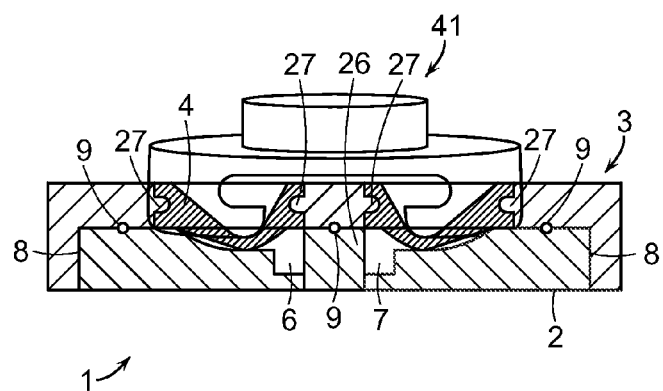

As shown in FIG. 5, the cover 3 comprises a recess 8 into which the base 2 is inserted. The positive-fit guarantees that the relative position of cover 3 and base 2 is defined. When assembling cover 3 and base 2, it is possible to minimize manufacturing tolerances, so that a plurality of pump modules can be produced, all having basically the same properties. Alternatively, it is also possible that the base 2 has a recess into which the cover 3 is inserted or engages in a form-fit manner, or cover 3 and base 2 each have at least one recess in which the other element engages in a form-fit manner. In this embodiment, the rear surface of the cover 3 comprises a rectangular recess into which the base, which has a corresponding rectangular outside shape, is inserted.

Base 2 and cover 3 are produced from a solid material, preferably plastic material, in particular thermoplastics. For example, materials to be used include POM (polyoxymethylene), PC (poly carbonate) or COC (cyclic olefin copolymer). Here base 2 and cover 3 are produced as one-piece, in particular integrally formed injection-molded parts. Base 2 and cover 3 consist of the same material, making it possible to produce in a simple and inexpensive manner a adhesively joined connection between base 2 and cover 3. Preferably, the connection is made by a welding process, for example, an ultrasound welding process or a laser welding process. In the case of a laser welding process, it is preferred that either the base 2 or the cover 3 is transparent while the other component is absorbent for the laser beam, at least in the welding area. However, the base 2 and the cover 3 can be joined also by other connection methods, for example, by gluing or clamping.

Preferably, the membrane 4 consists of one piece (see second embodiment, FIGS. 6, 7), or it is integrated in the cover 3 (as, for example, in the first embodiment described here). Preferably, the membrane 4 consists of one piece. Preferably, the membrane 4 comprises an elastomer, preferably a thermoplastic elastomer, for example, an EPDM (ethylene propylene diene rubber), ethylene propylene rubber or silicone rubber. The membrane 4 and cover 3 of the first embodiment of the pump module 1 are produced by means of a 2-component injection-molding process (2 component injection-molding).

The materials used for the base 2, cover 3 and membrane 4 are inexpensive and can be processed very precisely. As a result, the pump module 1 can be produced in an inexpensive manner, with reproducible measurements and maximum durability. Furthermore, as subsequently described, it is possible to integrate in an inexpensive and space-saving manner several functions in the pump module 1.

In addition, the pump module comprises a seal 9 (see FIG. 5). The seal is arranged between the base 2 and the cover 3. The seal 9 seals the fluid-leading areas of the pump module 1 toward the outside area. The seal 9 surrounds the pump channel 5, the pressure measuring chamber 10 and the valve unit 12 (see also FIG. 16). Here, the seal 9 is formed by a sealing lip. The sealing lip can be molded to the cover 3 or the base 2, or it can be loosely arranged. It is preferred that the sealing lip is injection-molded by means of 2-component injection-molding, for example, that it is injection-molded to the cover 3 in the production process of the membrane 4. In the previously mentioned case, preferably the sealing lip consists of the same material as the membrane 4. Alternatively, the sealing lip or part of the sealing lip can be injection-molded to the base 2.

Alternatively, it is possible to use one or several sealing rings or any other sealing agents instead of the sealing lip.

In the case in which the base 2 and the cover 3 are connected by welding, in particular by laser welding, the seals can also be produced during the welding process. In the process, the fluid-leading areas are traced in such a way that they are sealed the welding line toward each other and to the outside area.

The cover 3 and the base 2 form a pressure measuring chamber 10 (see FIGS. 24-27). The cylindrical recess 25 of the base 2 (see FIG. 2) merges with a respective diameter into a cylindrical recess of the cover 3. The cylindrical recess of the cover 3 is connected with an outlet passage which is also formed by the cover 3. The fluid can leave the pump module 1 by means of said outlet passage.

The pressure measuring chamber 10 comprises a flexible wall section 11 which can be deformed by the pressure of a fluid exerted in the pressure measuring chamber 10. During operation of the pump module 1, each pump cycle produces with a fluid a deformation of the wall section 11. The degree of deformation of the wall section 11 indicates the pressure in the pressure measuring chamber 10, at the same time indicating the pressure of the fluid. In particular, it is possible to detect excess pressure, which occurs, for example, in case of a downstream occlusion, or loss of pressure, which occurs when a line or tube connected with the pump module 1 is damaged. Furthermore, it is possible, when the pump module 1 is connected with a fluid-containing bag (which is a usual application), to detect by means of a pressure measurement whether the bag is empty. As shown in this embodiment, the pressure measuring chamber 10 can be arranged outside of the pump channel 5, or it can be arranged between the pump channel inlet 6 and the pump channel outlet 7. It can be part of the pump channel 5 or can be connected with the pump channel, for example, by means of a passage. The variations mentioned last make it possible to measure pressures upstream, as well as downstream, which can be used to detect an occlusion, a tubing failure or an empty bag.

It is also possible to measure the pressure inside the pump channel 5 or a section of the pump channel 5 when the pump channel inlet 6 and the pump channel outlet 7 are closed simultaneously. Especially in a case in which the pump channel 5 has a small volume, it is possible, for example, by comparing the pressures measured with reference values, to draw conclusions with regard to the fluid volume in the pump channel 5 and the presence of bubbles in the fluid, especially air bubbles the size of the pump channel or larger. In this way, it is possible to replace in an inexpensive manner established measuring methods of air detection, such as measuring the loss of an ultrasound wave passing through the fluid.

Alternatively or additionally, it is also possible to arrange two pressure measuring chambers 10 in front or behind the pump channel 5, to be able to measure pressures upstream and downstream. For example, in this way, it is possible to detect an empty fluid bag. Furthermore, it is possible to detect individual air bubbles in the fluid or occlusions located downstream or upstream.

In this embodiment, the flexible wall section 11 is designed as a membrane which, according to the invention, is preferred. Above the pressure measuring chamber 10, the cover 3 comprises a circular recess in which the flexible wall section 11 is arranged. Preferably, the flexible wall section consists of the same material which is preferably used for the membrane 4. For purposes of an inexpensive production, it is especially preferred to produce the flexible wall section 11 and the membrane 4 in a single process, in particular as part of a 2-component injection-molding process in the context of producing the cover 3. At the inside surface of the recess for the flexible wall section 11, the cover 3 comprises a projection which is encompassed on its upper and lower side by the flexible wall section, resulting in an increased connection between wall section 11 and cover 3.

Alternatively and additionally, it would be possible to provide the flexible wall section 11 in the base 2. The recess for the flexible wall section 11 in the cover 3 would be provided correspondingly at the bottom of the base 2.

The flexible wall section 11 can be directly accessed from the outside. Therefore, it is possible to determine a deformation of the wall section 11 without being obstructed by other components of the pump module 1. In this embodiment, the non-deformed flexible wall section 11 forms a planar surface with the surface of the cover 3.

Alternatively and additionally, it is possible to measure the pressure of the fluid by means of the membrane 4. In this way, it is possible to determine the pressure inside the pump channel 5.

Figure 28:
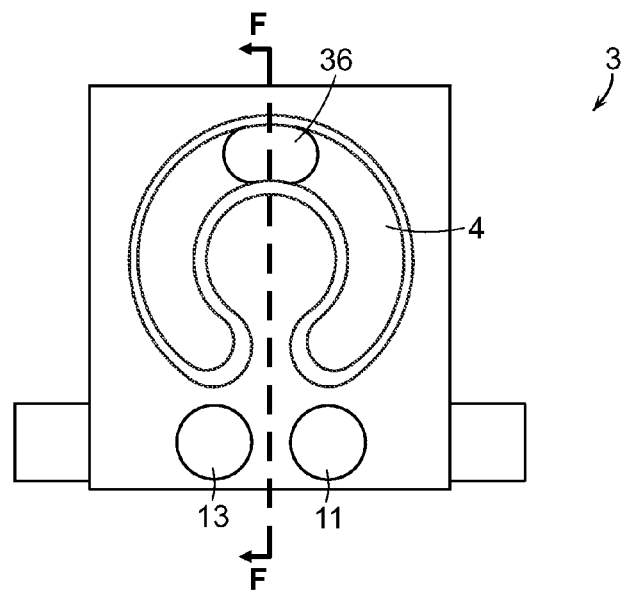
Figure 29:
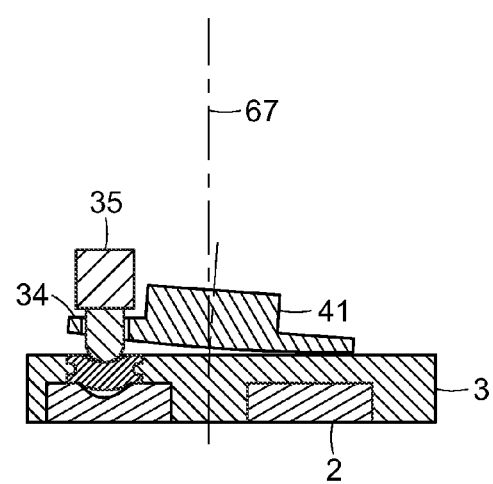

FIGS. 28 and 29 show an embodiment which depicts a device in which the pressure inside the pump channel 5 is measured by means of the membrane 4.

In a section opposite the membrane 4, the wobble device 41 has a recess 34 which comprises a pressure measuring device 35, here a movable, flexibly pretensioned rigid finger for measuring which is connected with a pressure sensor (not shown). The deformation of the membrane 4 is detected by means of the pressure measuring device 35 and used for determining the pressure inside the pump channel 5. When a membrane 4 having a bulge is used (for example, see FIGS. 8 and 10), preferably the bulge is interrupted in a measurement range 36 (see FIG. 28) in which the pressure measuring device contacts the membrane 4, to increase the sensitivity of the pressure measurement. Besides changing the thickness and/or the form of the wall, it is possible additionally or alternatively to design the membrane 4 in this area from a different material, for example, a material with increased elasticity.

Here, the pressure measuring device 35 is disconnected from the oscillation movement of the wobble device 41. It is solidly mounted in the housing of the wobble pump base module 40, to minimize the amplitude of the finger for measuring in relation to the membrane 4. Alternatively, it is also possible to integrate the pressure measuring device 35 at least partially in the wobble device 41.

In this way, depending on the periodically rotating contusion of the membrane 4, it is possible to measure inside the pump channel 5 the pressure downstream, upstream and when the inlet 6 and outlet 7 are closed.

In the embodiment shown, the pump module 1 comprises in addition to the pressure measuring chamber 10 a valve unit 12. The valve unit 12 is connected with the pump channel 5, making it possible to transport a fluid through the pump channel 5 and valve unit 12. The connection between pump module 5 and valve unit 12 is made by means of the pump channel inlet 6 (see FIG. 2 and FIG. 24). The pump module 1 comprises a flexible valve body 14 which is arranged in the valve unit 12. The valve body can occupy an idle position in which the valve body 14 closes the valve unit 12 to prevent fluid from passing through (see FIG. 24 or FIG. 26), or the valve body can occupy an operation position in which the valve body 14 allows the fluid to flow through the valve unit (see FIG. 25 or FIG. 27). A first wall section 13 of the valve unit 12 has a flexible design and interacts with the valve body 14 so that the valve body can be brought in operation position through a deformation of the first wall section 13, making it possible that fluid flows through the valve unit 12.

In idle position, the valve body is resiliently pretensioned against a stop position 19 of the valve unit. As a result, a specific minimum pressure is required for the valve body 14 to leave the idle position and for the valve to open. The pretension is adjusted in such a way that the fluid must have a minimal pressure of ≥2 bar, preferably a minimal pressure of 1≥bar, to push the valve body 14 away from the stop position 19. Consequently, the pump module 1 is closed in its basic position. Only when the valve body 14 is activated, it is possible to transport a fluid through the pump module 1. The valve makes sure that a fluid does not pass the pump module when it is not desired, for example, that fluid is not discharged unwantedly from a bag when the bag is connected to the pump module 1. Such a valve is also called an anti-free-flow-valve. Furthermore, the resilient pretension of the valve body 14 has the effect that the valve body 14 is pressed into idle position, whereupon the valve body 14 returns into idle position when the pressure of the fluid or the first wall section 13 on the valve body 14 is reduced.

If by means of the pump module 1a fluid is transported in reverse direction, or the pump module 1 is operated in opposite flow direction, which explicitly represents a possible use of the pump module 1, the valve body 14 is pressed against the stop position 19, and thus into idle position, not only by the pretension of the valve body 14 but also by the fluid itself. As a result, the valve remains closed when it is not forcibly opened, independent of the pressure of the fluid.

Figure 24:
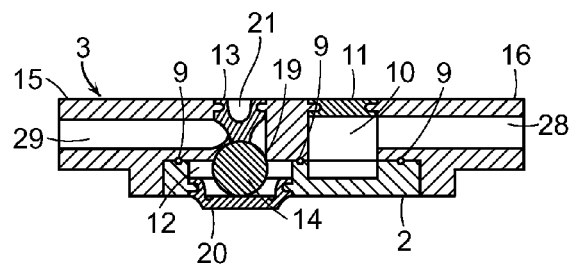
Figure 25:
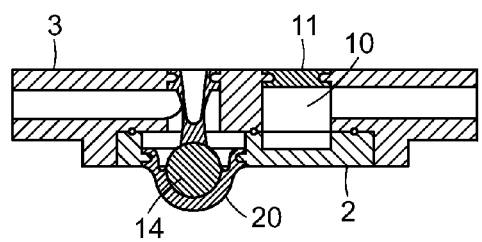
Figure 26:
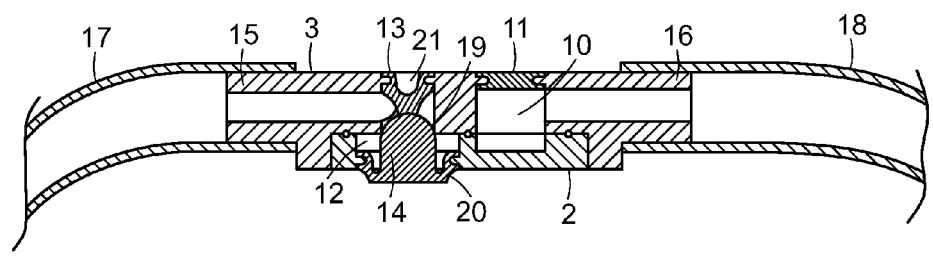
Figure 27:
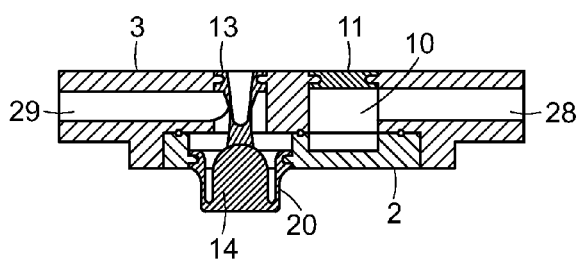

The valve unit 12 comprises a second wall section 20, wherein the second wall section 20 can be flexibly deformed. The second wall section 20 is actively connected with the valve body 14 and resiliently pretensions the valve body 14 against the stop position 19. In a first model, which is depicted in FIGS. 24 and 25, the second wall section 20 and the valve body 14 consist of two pieces. In a second model, which is depicted in FIGS. 26 and 27, the second wall section 20 and the valve body 14 consist of one piece, in his case even formed integrally.

Preferably, the first wall section 13, the second wall section 20 and the valve body 14 are designed from semi-rigid or soft flexibly deformable materials. Preferred materials include thermoplastic plastic materials, thermoplastic elastomers or silicone-containing materials. In particular, it is possible to use the same materials that are used for producing the membrane 4, the flexible wall section 11 of the pressure measuring chamber 10 or the sealing lip 9. In this way, the number of different materials and the number of process steps for producing the pump module 1 can be reduced, resulting in the fact that the pump module 1 can be produced in a more cost-effective manner. In particular, the first wall section 13 and the second wall section 20 can be produced as part of a 2-component process with a further component of the pump module 1, particularly with the base 1 or with the cover 3.

In this embodiment, the valve unit 12 is formed by a cylindrical recess 24 of the base 2 (see FIG. 2), which merges with a reduced diameter into a cylindrical recess of the cover 3. The cylindrical recess of the cover 3 is connected with an inlet channel 29, which is also formed by the cover 3, and by means of which the fluid can enter the pump module 1 (see FIG. 24).

Above the valve unit 12, the cover has a round recess in which the first flexible wall section 13 is arranged. At the inside edge of the recess, the cover 3 comprises a projection which is encompassed on both sides by the flexible wall section 13, thus improving the durability of the connection between the first wall section 13 and the cover 3.

Below the valve unit 12, the base 2 has a round recess in which the second wall section 20 is arranged. At the inside edge of the recess, the base 2 comprises a projection which is encompassed on both sides by the second wall section 20, thus improving the durability of the connection between the second wall section 20 and the base 2.

The stop position 19 is formed by a step which is created in that the cylindrical section of the valve unit 12 in the base 2 has a larger diameter than the cylindrical section of the valve unit 12 in the cover 3.

The valve body 14 is arranged in the area of the valve unit 12, which is located in the base 12. The second flexible, elastic wall section 20 is already deformed when the valve body 14 is in idle position, which increases the contact pressure that presses the valve body 14 like a seal against the stop position 19. By means of a deformation of the first wall section 13, preferably in a deformation direction pointing in the direction of the valve body 14, in this case vertically to the level of the first wall section 13 and the cover 3, the valve body 14 can be transferred to operation position (see FIG. 25 and FIG. 26). As the valve body 14 transfers to operation position, the second flexible wall section bulges more and more to the outside. After reducing the pressure on the first wall section 13, the reset forces of the second wall section 20 result in the fact that the valve body 14 returns to idle position.

In this embodiment, the first wall section 13 is designed as part of the outside wall of the pump module 1, so that the first wall section 13 can be operated from the outside without obstruction. The second wall section 20 is also designed as part of the outside wall of the pump module 1. As a result, it is possible top produce a pump module with a compact size.

The first wall section 13 comprises a depression 21 for the engagement of a projection 51, for example a bolt or a bar, which depression can be accessed from the outside. In this way, it is possible to prevent a misuse of the valve, in particular an unintentional opening of the valve. Furthermore, such a depression can be used as a positioning aid, to connect in a correct position the pump module with a wobble pump base module. Alternatively, the first wall section 13 can also be designed in other forms, for example, planar or as an elevation above the surface of the cover 3. The latter variation allows for a simple manual operation of the valve, which is advantageous when it is required to open the valve when the pump module is not yet connected with the wobble pump base module.

Alternatively, it is possible to switch the functions of base 2 and cover 3, i.e., the second wall section 20 and the valve body 14 can be arranged in the cover 3 and the first wall section 13 can be arranged in the base 2. Even the inlet channel 29 and the outlet channel 28 can be formed partially or completely by the base 2. Basically, it is possible to use also other shapes of the valve unit 12 and/or the pressure measuring chamber 10, for example elliptic or rectangular shapes.

The valve unit 12 described is not only suitable to be used in combination with a pump channel 5, which is formed by means of a membrane 4, but basically it can also be used with other pump systems. For example, it is possible to use a flexibly deformable tube as a pump channel 5. Furthermore, the invention-based structure of the valve unit 12 can be used independently from the pumping principle. For example, the invention-based structure of the valve unit 12 can be part of a linear, peristaltic finger pump, roller pump or membrane pump. The same applies to the pressure measuring chamber 10, in particular in combination with the valve unit 12. A special advantage of the combination of a pump principle using a membrane with the valve unit 12 and the pressure measuring chamber 10 is that individual elements of the pump module can be provided with several functions, making it possible that the pump module 1 can be produced in an inexpensive manner, in a compact form and with high mechanical precision.

The cover 3 comprises a first connector 15 and a second connector 16 for connecting a tube. The first connector 15 is connected with the pump inlet 6, the second connector 16 is connected with the pump outlet 7. In this embodiment, the first connector 15 and the second connector 16 are designed as tubular adapters, each of which can be covered with a tubing section (see FIG. 26), and can optionally be adhesively joined to the adapter for the purpose of improving the stability of the connection, for example by gluing or welding. A section of the inlet channel 29 is formed with the first connector 15, a section of the outlet channel 28 is formed with the second connector 16. Consequently, after passing through the inlet channel 29, a fluid that is injected into the pump module 1 by means of the inlet channel 29 passes through the valve unit 12, the pump channel inlet 6, the pump channel 5, the pump channel outlet 7 and the pressure measuring chamber 10 before leaving the pump module by means of the outlet channel 28.

It is also possible that a fluid passes through the pump module 1 in a different direction. In this case, the valve of the pump module 1 forms a stop valve which stops the flow of the fluid to the inlet channel 29 independent of the pressure of the fluid and which releases the flow by activating the valve body 14 by means of the first wall section 13. Alternatively, the first connector 15 and/or the second connector 16 can be designed in other shapes, for example, in the form of a sleeve in which a tubing section can be inserted.

The pump channel 5 can have a genuine circular design, or it is designed in a way that differs from a genuine circular design like the pump modules 1 shown in embodiments. In this way, it is possible to prevent the undesired condition that during operation of the pump module 1 a short-term open connection (a "short") exists in which the fluid can pass through the pump channel 5 unhindered or not sufficiently hindered.

Figure 2:
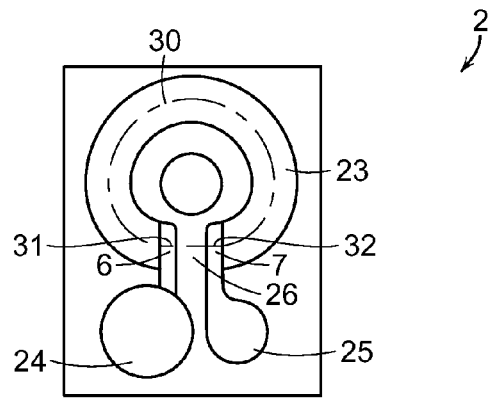

For example, the first embodiment of the pump module 1 shown in FIGS. 1 and 2 comprises a pump channel 5 which has a circular section 30, a first straight section 31 and a second straight section 32. The circular section is arranged between the first straight section and the second straight section. The pump channel inlet 6 is situated in the first straight section 31, the pump channel outlet 7 is situated in the second straight section 32. Because of the fact that the first section 31 and the second section 32 have a straight design, an embodiment is achieved in which by means of a wobble device 41, for example, indicated by a wobble plate (shown in FIG. 3), the pump channel 5 can be almost simultaneously sealed at the pump channel inlet 6 and the pump channel outlet 7 (see FIG. 5). Preferably, the first section 31 and the second section 32 are arranged in parallel or collinear manner, wherein the collinear manner is depicted in the pump module 1 shown FIGS. 1, 2 and 5.

Figure 3:
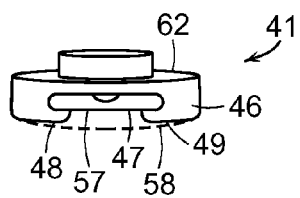
Figure 4:
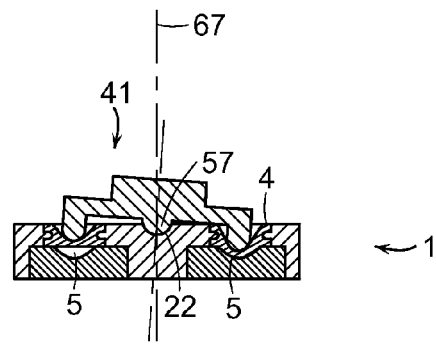

By means of a wobble device 41 mounted in axially movable fashion along its rotational axis or a wobble device 41 having a flexibly rebounding design at least in the areas compressing the membrane 4, it is possible to improve the simultaneous closing of pump channel inlet 6 and pump channel outlet 7, as well as the overall pump process. In this case, sufficient contact pressure can be achieved by means of an axial displacement or deformation of the wobble device. In particular, the axial bearing and/or the flexibly rebounding design of the wobble device 41 can guarantee that during a pump cycle the wobble device 41 sufficiently presses the membrane 4 by means of an axial movement in each phase of the cycle, even when the wobble device 41 has a gap, as shown in FIG. 3. For the purpose of an axial displacement, the wobble device 41 can be axially pretensioned.

Figure 8:
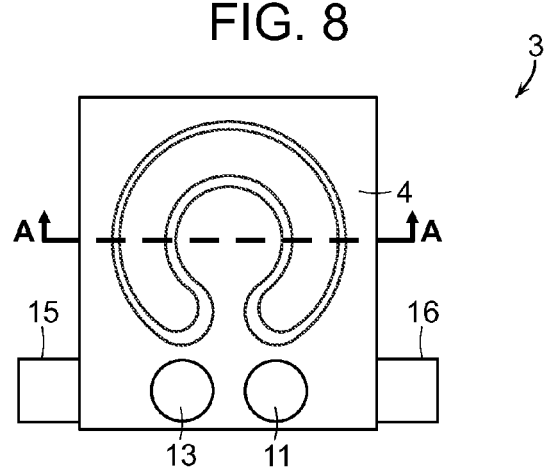
Figure 9:
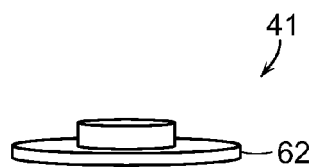
Figure 10:
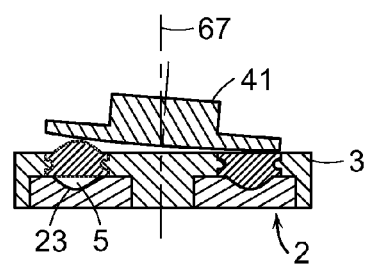

FIGS. 8 and 10 show a third embodiment of an invention-based pump module 1. Contrary to the first embodiment in which the membrane 4 does not protrude beyond the cover 3, the membrane 4 is designed with a bulge. In non-deformed condition, the lower surface of the membrane 4 facing the groove 23 is formed in such a way that the pump channel 5 can be securely closed. In this embodiment, the lower surface has a planar design. The upper surface of the membrane 4 has a toric design and protrudes beyond the cover 3. For example, by means of a wobble device 41, such as the one shown in FIG. 9, it is possible in a section of pump channel 5 that the membrane 4 can be pressed in fluid-tight manner against the surface of the groove 23 through the pressure of the wobble device 41 on a section of the toric area of the membrane 4. As a result, a fluid can be transported through the pump channel through a wobble movement of the wobble device 41 about a tumble axis 67. Because of the toric membrane 4, the lower surface of a base 62 of the wobble device 41 facing the membrane 4 can have a planar design (see FIG. 10). FIG. 10 shows the membrane 4 with a section that is not deformed and a section that is deformed by the wobble device 41 and that closes the pump channel 5. In the remaining design, the third embodiment corresponds to the first embodiment of the pump module 1. Such a planar embodiment of a wobble device 41 is advantageous in that the wobble device 41 and the drive unit of the wobble device are insensitive to lateral tolerances. Furthermore, the wobble device 41 can be designed in a simple and defined manner as a semi-rigid or flexible plate (see FIG. 37). In this way, it is possible to realize an intrinsic flexibility of the wobble device 41, to achieve a defined contact pressure of the wobble device on the membrane. In this way, it is possible to compensate axial tolerances.

Figure 11:
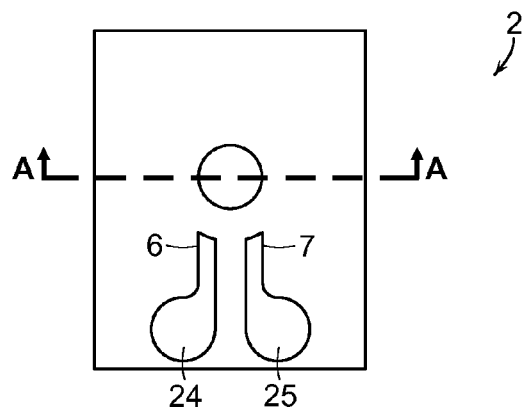
Figure 12:
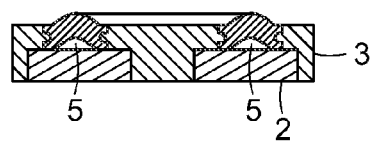
Figure 13:
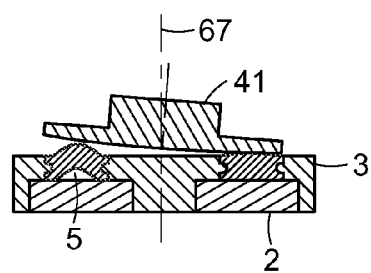

FIGS. 11 to 13 show a fourth embodiment of an invention-based pump module 1. Contrary to the first embodiment, the curved membrane 4 does not have a planar design. Its upper surface is designed with a bulge, corresponding to the third embodiment. In non-deformed condition, the lower surface of the membrane 4 is curved to the inside. Apart from the pump channel inlet 6 and the pump channel outlet 7 which are designed as groove-shaped cuts, the base has a planar design at its upper surface opposite the lower surface of the membrane 4. The upper surface (curved to the inside) of the lower surface of the membrane 4 and the planar surface of the base 2 form a pump channel 5 through which a fluid can be transported. For example, by means of a wobble device, such as the one shown in FIG. 9, in a section of the pump channel 5 the membrane 4 can be pressed in fluid-tight manner to the surface of the base 2. FIG. 13 shows the membrane 4 in a section that is not deformed, and a section that is deformed by the wobble device 41 and that closes the pump channel 5. In the remaining design, the fourth embodiment corresponds to the first embodiment of the pump module 1.

Figure 14:
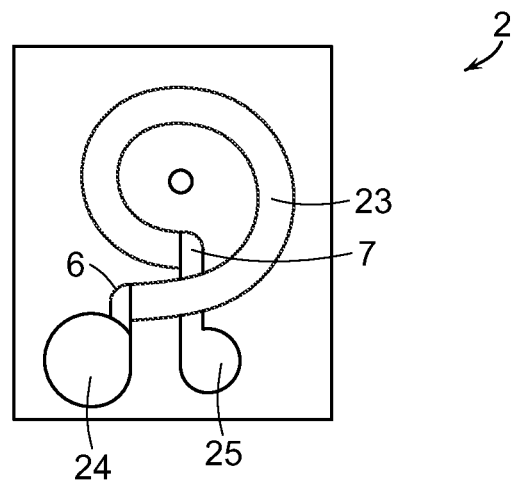
Figure 15:
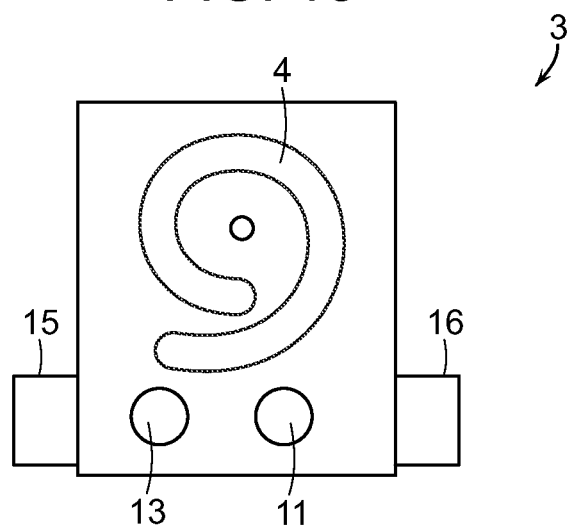

FIGS. 14 and 15 show a fifth embodiment of an invention-based pump module 1. Contrary to the first embodiment, the pump channel 5 between pump channel inlet 6 and pump channel outlet 7 has a spiral design, wherein in a section between pump channel inlet 6 and pump channel outlet 7 the pump channel 5 overlaps radially, i.e., the pump channel 5 covers an angular range of more than 36°. Preferably, the spiral-shaped pump channel 5 is designed in a plane vertically to the tumble axis. In the overlapping area, toward the pump channel inlet 6 and the pump channel outlet 7, the spiral-shaped section of the pump channel 5 merges into a straight section, respectively, wherein both straight sections are arranged in parallel fashion. Alternatively, the pump channel can also have a genuine spiral-shaped design. Otherwise, this embodiment of the pump module 1 corresponds to the first embodiment.

A spiral-shaped section in the pump channel 5 makes it possible to arrange pump channel inlet 6 and pump channel outlet 7 offset to one another, so that in one section the pump channel can overlap radially (see the figures). The overlap makes it possible to guarantee by means of a wobble device 41 that, in the context of oscillation, the pump channel inlet 6 and the pump channel outlet 7 can be securely closed. As a result, a situation can be prevented in which the pump channel 5 is opened for only a moment between pump channel inlet 6 and pump channel outlet 7. Furthermore, the overlap of the pump channel 5 makes it possible to produce during the tumbling process a compression of the fluid inside the pump channel 5, preferably by locally closing the pump channel 5, starting with the pump channel inlet 6, while in the section of the pump channel outlet 7 the circulating deformation of the membrane 4 has not yet reached the pump channel outlet 7. In the case of continued oscillation, the volume between these two sealed areas of the pump channel 5 is reduced because the local deformation sealing the pump channel 5, which is further away from the center (which is preferably located on the tumble axis), covers a larger distance than the deformation situated on the inside. The compression phase ends when the deformation situated on the inside reaches the pump channel outlet 7. Such compression can be performed by means of the wobble device 41 shown in FIGS. 18 to 20, or when the membrane 4 is provided with a respective bulge, such compression can be performed with the wobble device shown in FIG. 9.

Figure 16:
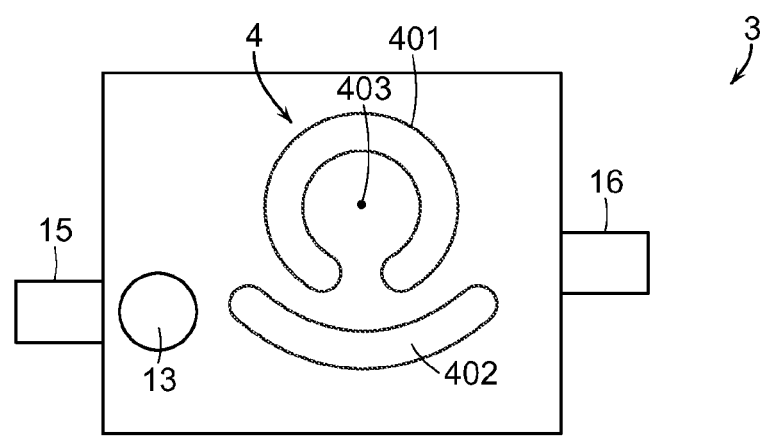
Figure 17:
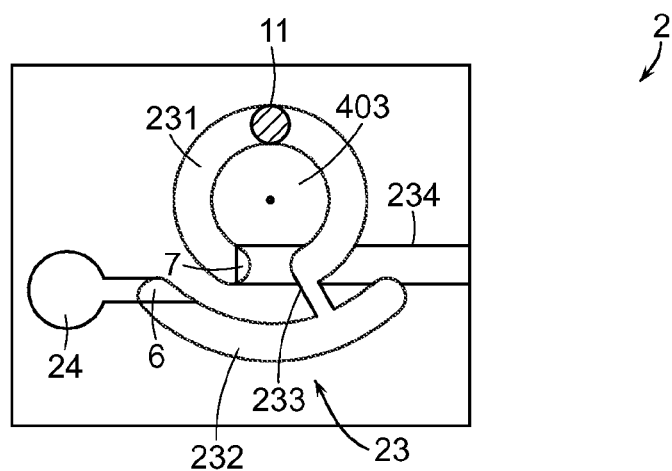

FIGS. 16 and 17 show a sixth embodiment of an invention-based pump module 1. Contrary to the first embodiment, the pump channel 5 comprises two circular pump channel sections which are formed in the base 2 by two circular membrane sections 401 and 402 forming the membrane 4 and by two circular groove sections 231 and 232, wherein the first pump channel section is arranged in a first radius toward a center 403 (which is preferably located on the tumble axis), and the second pump channel section is arranged in a second, here larger, radius toward the center 403, which radius differs from the first radius. The first pump channel section extends over an angular range of preferably at least 180° to at the most 355°. Preferably, the second pump channel section extends over an angular range of at least 20°. Preferably, the first pump channel section and the second pump channel section overlap in an angular range of at least 10°.

The pump channel inlet 6 is arranged at one end of the second, outside groove section 232. The pump channel outlet 7 is arranged at one end of the first, inside groove section 231. The second pump channel section/the second groove section 232 is connected by means of a short transition duct 233 with the first pump channel section/the first groove section 231. The transition duct 233 runs from a place of the second pump channel section located at a distance from the pump channel inlet 6 to the end of the first pump channel section located opposite of the pump channel outlet 7. Because of the fact that the transition duct 233 is located before the end located opposite of the pump channel inlet 6, the pump channel 5 is split at the place of the transition duct 233 into a first pump channel section (start of the transition duct 233 to the pump channel outlet 7) and a second pump channel section (start of the transition duct 233 to the end of the second pump channel section located opposite the pump channel inlet). In the first pump channel section, the fluid is transported to the pump channel outlet 7. In this embodiment, the second pump channel section, which forms a "dead end" for the fluid, is used for pressure compensation.

The pressure compensation takes place as follows: in a first periodically repeating phase of the tumbling process, the area of the pump channel inlet 6 in the outside second pump channel section and an area in the inside first pump channel section of the pump channel 5 located before the pump channel outlet 7 are sealed simultaneously. With advancing oscillation, which takes place counter-clockwise in the embodiment shown, a phase of compression follows because the radius of the inside first pump channel section is smaller than the radius of the outside second pump channel section. As a result of the flexibility of the membrane 4, at least partially through deformation of the membrane 4, excess pressure is compensated through the second pump channel section between transition duct and the end of the second pump channel section facing away from the pump channel inlet 6. Ultimately, with advancing oscillation, the transition duct 233 is crossed, the deformation of the membrane 4 is continued in the first pump channel section, resulting in the fact that excess pressure formed in the second pump channel section can be released. Preferably, the membrane 4 is compressed simultaneously in the area of the inlet and outlet of the transition duct 233 when the transition duct 233 is reached. In this way, it is possible to prevent an undesired backflow of the fluid at the transition of the membrane 4, which is deformed through oscillation, from the second pump channel section to the first pump channel section.

As a variation in the second pump channel section, the membrane can be provided with a different material thickness and/or designed from a different material which allows the pressure compensation to be optimized.

The transition duct 233 is formed in a plane of the base 2 which is located in the plane in which the groove 23 is located. From the pump channel outlet 7, a supply duct 234 situated in a plane below the plane in which the groove is located leads to a second connector 16. It is also possible to design other embodiments of the transition channel section 233 or the supply duct 234.

In an alternative model, the first and/or the second pump channel section can have a spiral-shaped design instead of a circular design.

Wobble devices can include wobble devices 41 having a bar or wobble device 41 having a planar contact surface in case the membrane is to be designed with a bulge.

According to a sixth embodiment of a pump module 1, the pressure measuring chamber 10 is located in the area of the pump channel 5 between the pump channel inlet 6 and the pump channel outlet 7, here in the first inside pump channel section. The pump channel 5 is used as a measuring chamber. The flexible wall section 11 of the pressure measuring chamber 10 for measuring the pressure forms part of the wall of the pump channel 5. The flexible wall section 11 is located opposite of the membrane 4.

A fluid inside the pump channel 5 can be measured downstream and upstream, even in a situation when pump channel inlet 6 and pump channel outlet 7 are closed simultaneously. In this way, it is possible to detect occlusions, tubing failures or empty bags. Furthermore, such pressure measurements make it possible to detect air bubbles in the fluid, especially air bubbles the size of the pump channel 5 or larger. It is also possible to determine the filling volume of a fluid in the pump channel 5 when the pump channel inlet and pump channel outlet are closed.

Alternatively, the measuring chamber 10 can be detached from the pump channel 5 and connected with the pump channel 5 by means of a supply line.

Figure 21:
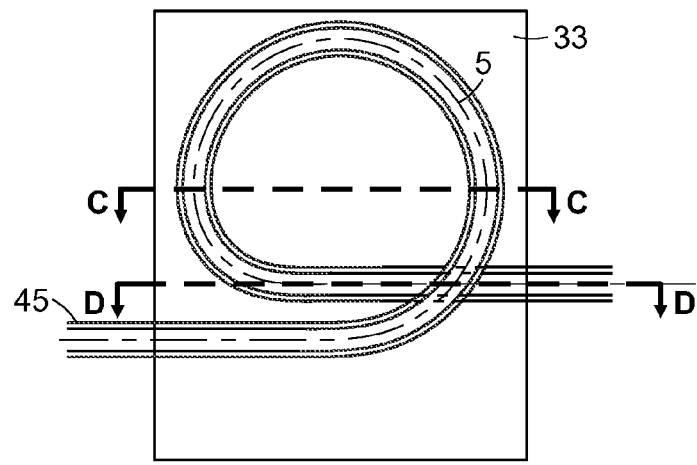
Figure 22:
Figure 23:
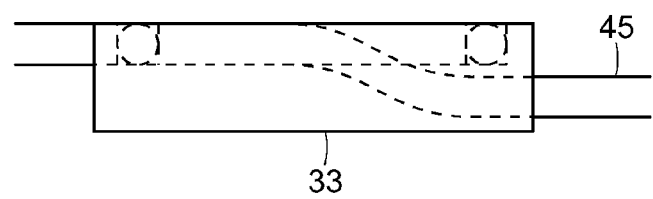

In an alternative seventh embodiment (different variations are shown in FIGS. 21 to 23), the pump channel 5 is formed by the section of a flexibly deformed tube 45. The pump channel 5 has a spiral-shaped section which merges on both sides into a straight section, respectively, wherein both straight sections are arranged offset to one another. The straight section of the tube 45 located on the inside passes under spiral-shaped section (see FIG. 23). In this embodiment, the tube 45 is arranged in a groove-shaped duct of a rigid carrier 33, which fixes the tube 45 in its form. For example, it is possible to use resilient, flexibly deformable tubes 45 that are usually used for peristaltic flexible-tube pumps.

The pump channels 5 of the pump module 1 shown in the embodiments have a cross-section which, in the section between pump channel inlet 6 and pump channel outlet 7, comprises a value ranging from $0.1 \text{ mm}^2 \leq Q \leq 10 \text{ mm}^2$, preferably ranging from $0.5 \text{ mm}^2 \leq Q \leq 2 \text{ mm}^2$. Furthermore, the volume VS of the pump channel 5, in the section between pump channel inlet 6 and pump channel outlet 7, comprises a value ranging from $1 \text{ µl} \leq VS \leq 500 \text{ µl}$, preferably ranging from $10 \text{ µl} \leq VS \leq 100 \text{ µl}$. The base 2 and the cover 3 rigidly connected with the base 2 comprise together a length and width of 100 mm at the most, preferably 50 mm at the most, especially preferred 25 mm at the most, and a thickness of 20 mm at the most, preferably 10 mm at the most, especially preferred 5 mm at the most.

Besides a wobble pump drive system 43, the wobble pump base module 40 comprises a wobble device (already mentioned) by means of which the membrane 4 can be compressed. At the same time, the geometry of wobble device 41 is adapted to the pump channel 5. In this case, the wobble device 41 comprises a line-shaped bar that is curved at least in sections and that can be oscillated to deform in wobbling manner the membrane 4, wherein the bar 46, as well as the pump channels 5 of the pump module 1 in the embodiments described are designed in a way that differs from a genuine circular design.

Alternatively, the bar 46 can also have a circular design, wherein in this case the wobble device 41 is preferably mounted in axially movable fashion or the wobble device 41 has a resilient design (see FIG. 3).

The bar 46 is mounted to a disc-shaped base 62 of the wobble device 41 which in this way is designed as a wobble plate. Alternatively, the wobble device 41 can also be designed without a bar, having a planar pressure surface, in case the pump module 1 comprises a membrane 4 having a bulge.

According to a first embodiment of an wobble device 41, the bar 46 comprises a circular section 47, a first straight section 48 and a second straight section 49, wherein the circular section 47 is arranged between the first straight section 48 and the second straight section 49 (see FIG. 3). The course of the bar 46 corresponds to the course of the pump channel 5 of the first embodiment of the pump module 1 which is shown in FIGS. 1, 2, 4 and 5. The bar 46 does not have a completely circular design but is recessed in a section between the first straight section 48 and the second straight section 49. The recess has the purpose of bridging the bar 26 of the pump module 1 that separates the pump channel inlet 6 from the pump channel outlet 7.

In the first straight section 48 and the second straight section 49, the bar ends in the form of a rounded tongue, respectively. This tongue shape allows a resilient yield of the end sections of the first straight section 48 and the second straight section 49. In this way, it is possible to reduce by means of the wobble device 41 the impact of the membrane 4 in the area of the pump channel inlet 6 and pump channel outlet 7.

Basically, the bar 46 can be designed as having a consistent height, which here means that the edge of the bar 46 opposite of the pump module 1 is located in a plane. According to the first embodiment of the wobble device 41, the bar 46 is designed with a variable height, i.e., the edge of the bar 46 is not located in a mutual plane. In the area of the first straight section 48 and the second straight section 49, the height of the bar 46 is reduced in a curved manner (a dotted line 58 in FIG. 3 shows the course of the bar with a constant height). As a result, it is possible that during oscillation the wobble device 41 securely compresses simultaneously the pump channel inlet 6 and the pump channel outlet 7 of a pump channel 5 of a pump module 1 (see first embodiment), thus preventing backflow problems. Preferably, the wobble device 41 is mounted in axial fashion, for example flexibly, to guarantee that through an axial movement in the direction of the pump module 1 the pump channel inlet 6 and pump channel outlet 7 are securely sealed.

Figure 18:
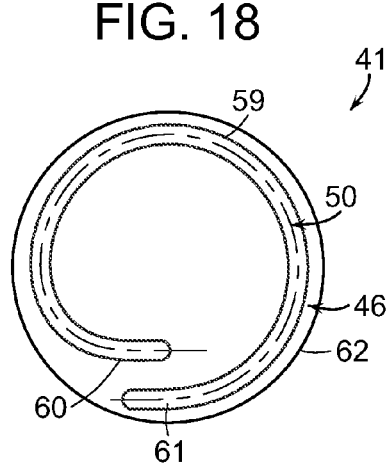
Figure 19:
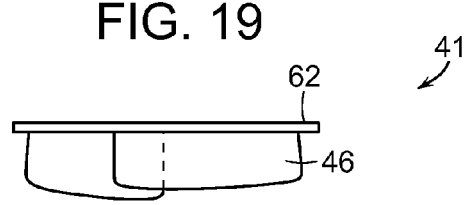

FIGS. 18 and 19 show tow models of a third already mentioned embodiment of an wobble device 41. In this embodiment, the bar 46 of the wobble device 41 comprises a spiral-shaped section 59 to which on both sides a respective straight first and second section 60, 61 is connected, wherein the straight sections 60, 61 are arranged parallel to one another, resulting in an overlapping of the bar 46. The course of the bar 46 corresponds to the course of the pump channel 5 of the fifth embodiment of the pump module 1 (see FIGS. 14, 15). In a first section of the spiral-shaped section, the bar 46 is higher than in a second section of the spiral-shaped section which is located further away from the center of the coil (see FIG. 19). In this embodiment, the height of the bar is increased when the radius of the coil decreases. The straight section 60, 61 is attached to the spiral-shaped section. Because of the fact that the bar 46 is higher in an area that is closer to the center, it can be guaranteed that the pump channel is always securely compressed.

Figure 20:
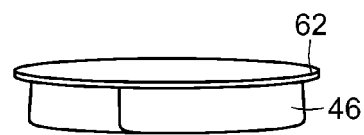

FIG. 20 shows a model of the second embodiment of the wobble device 41 shown in FIGS. 18 and 19.

Alternatively or additionally, it is possible to design the pump channel 5 of the pump module 1 with varying slope, or to vary the size of the membrane 4 or the height of its bulge depending on the oscillation center.

Preferably, the bar 46 of the wobble device 41 is a rigid body. In particular, materials to be used can include plastic materials or even metals. Preferably, the bar 46 is an injection-molded part. In particular, the bar 46 can be produced in one piece, with the base 62 being designed as a wobble plate. Furthermore, the bar can consist of a rigid material, but it can also consist of a semi-rigid material. Because of the intrinsic flexibility of the bar 46, it can be easier adapted to the membrane or groove profile, which can be of advantage in case of radial and/or axial tolerance compensations.

In a flat embodiment of the wobble device 41 shown in FIG. 9, which is designed as a wobble plate, preferably, the base 62 comprises a semi-rigid body.). Because of its intrinsic flexibility, it is possible to realize an axially resilient flexibility of the wobble plate. As a result, the contact pressure can be defined to achieve a secure, periodically rotating compression of the pump channel 5, and to guarantee especially the simultaneous closure of inlet and outlet. In addition, it is possible in this way to compensate axial tolerances between the pump base module and the pump module.

FIGS. 30 to 37 show different wobble pump systems which comprise a wobble pump base module 40 and a pump module 1.

Figure 33:
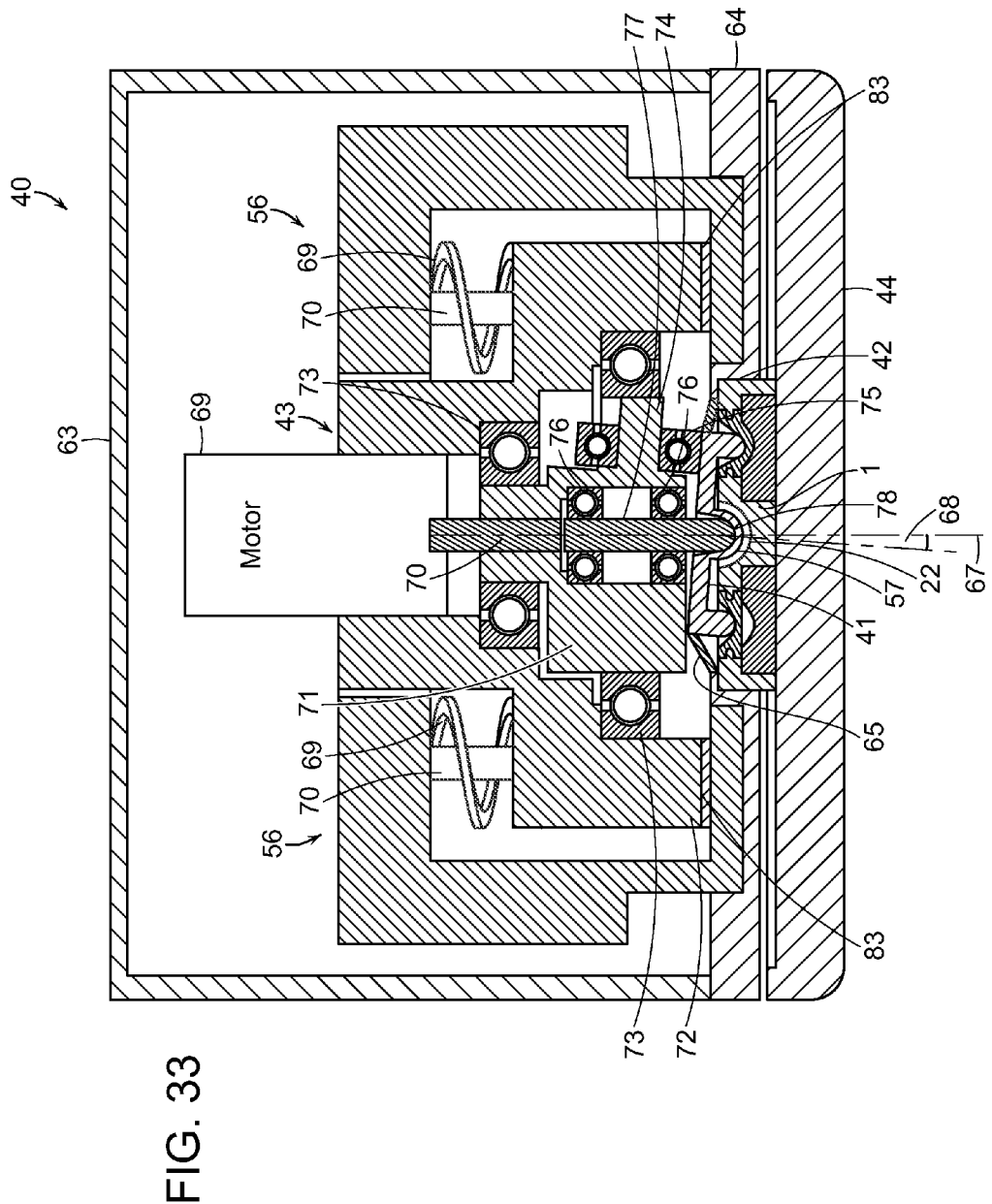

A wobble pump base module 40 comprises a wobble pump drive system 43 and a wobble pump device 41 (for example, see FIG. 33). By means of the wobble pump drive system 43, it is possible to activate the wobble pump device 41 to perform oscillation. Furthermore, the wobble pump base module 40 comprises a housing in which the wobble pump drive system 43 and the wobble pump device 41 are arranged. The housing comprises a top 63 and a bottom 64.

Figure 30:
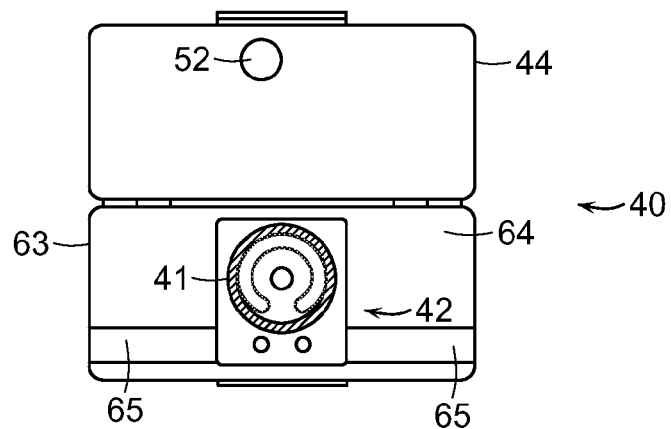
Figure 31:
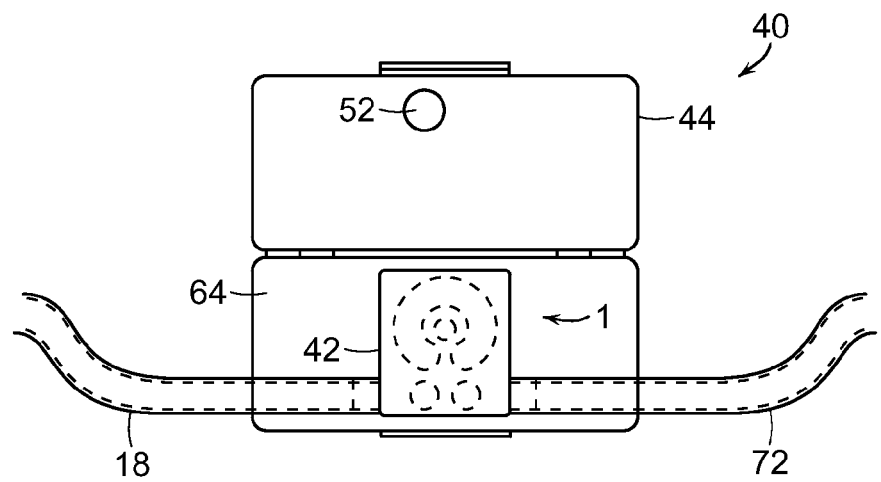

To receive the pump module 1, the wobble pump base module 40 comprises a receptacle 42 (see also FIGS. 30 and 31). The receptacle 42 is designed in such a way that the invention-based pump module 1 can be manually applied or inserted in the receptacle 42, and the pump module 1 can be manually removed from the receptacle 42. In this context, to insert or apply manual means that it is not required to use any tools for inserting or removing the pump module 1.

In this embodiment, the receptacle 42 is designed in the form of a depression or vat. The receptacle 42 corresponds to the outside shape of the pump module 1, so that the pump module 1 can be received by the receptacle 42 in form-fit manner. This is advantageous for correctly positioning the pump module 1 in relation to the wobble device 41. In this case, the receptacle 42 has a rectangular shape corresponding to the rectangular shape of the pump module 1. It is certainly also possible to use different designs for the pump module 1 and the receptacle.

At its bottom part, the receptacle 42 has a recess. The wobble device 41 is arranged in the area of the recess, so that the wobble device 41 can be actively connected with a pump module 1 inserted in the receptacle 42. Preferably, the gap between receptacle 42 and wobble device 41 is sealed in fluid-tight manner, for example, by means of a flexible membrane 65, to prevent that fluid, which has entered the receptacle 42, for example, through improper handling or a defective pump module 1, flows unwontedly into the inside of the housing of the pump base module 40.

Furthermore, in addition to the receptacle, the bottom of the housing 64 comprises two groove-shaped ducts 65 coming out of the receptacle 42. Sections of the tube coming out of both sides the pump module 1 can be inserted into the groove-shaped ducts 65.

By designing the pump module 1 at least partially in an asymmetric manner and corresponding with the receptacle 42, it can be guaranteed that the pump module 1 can be inserted in the receptacle in only one direction. In this way, it is possible to reduce the risk of an incorrect use. In this case, the tube nozzles 15, 16 of the pump module 1 are not arranged in the center but offset from the center of the pump module 1.

The receptacle 42 can be designed as part of the housing. In the embodiment, the receptacle 42 is formed by the bottom of the housing 64.

Furthermore, the wobble pump base module 40 comprises a securing device by means of which the pump module 1 can be secured in its position in the receptacle 42. The securing device can be operated manually, i.e., without the use of tools, which means that it can be operated in a simple and uncomplicated manner.

In this embodiment, the securing device comprises a cover 44. The cover 44 is hinged to the housing, here to the bottom of the housing 64. The receptacle 42 can be closed by means of the cover 44. When the cover 44 is closed, the cover 44 secures in form-fit manner the pump module 1 in its position in the receptacle 42 (for example, see FIGS. 22 and 23). When the cover 44 is opened, the pump module 1 can be manually removed from the receptacle 42.

It is possible to use known devices for securing the cover 44 in its closed position. For example, it is possible to use snap-on, latch or any other locking mechanisms. The cover can be also secured by means of an automatically controlled locking system (possible in addition), to prevent that the cover 44 is opened while the pump is operated.

Furthermore, the wobble pump base module 40 comprises a valve actuator. The valve actuator is designed in such a way that it deforms the first flexible wall section of the valve unit 12 of the pump module 1 when the pump module 1 is applied or inserted, thus bringing the valve body 14 in operation position.

Figure 32:
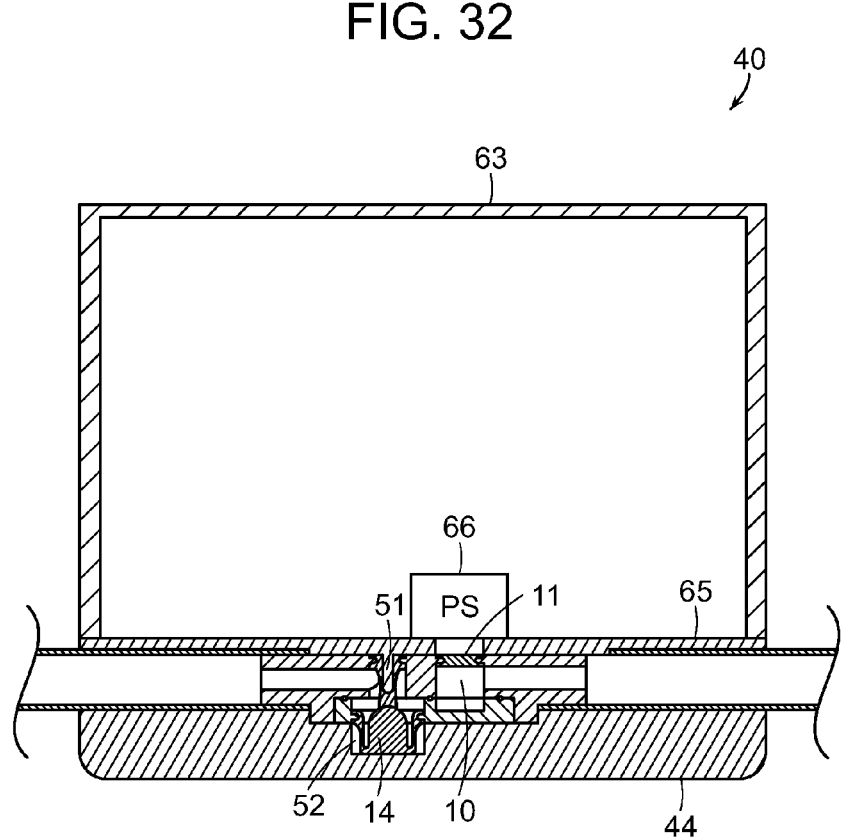

In this embodiment, the valve actuator is designed by a rigid, protruding bolt 51 (see FIG. 32). The bolt 51 is inflexibly arranged at the bottom of the receptacle 42. The bolt 51 is designed to engage in the depression 21 of the pump module 1 (see also FIG. 24). When the pump module 1 is inserted, the bolt engages in the depression 21, deforms the first flexible wall section 13, thus bringing the valve body 14 in operation position. Depending on the design of the first flexible wall section 13 and depression 21, the valve actuator can have a different form, for example, it can be designed as a bar or, when the membrane 13, instead of being designed with a depression or flat with an elevation, comprises a depression or recess into which the elevation of the membrane 13 engages when the pump module 1 is inserted.

Alternatively, it is also possible to provide as a valve actuator a movable projection, instead of a rigid projection, such as a rigid bolt or bar (not shown). In this way, it is possible to activate the valve body 14 for opening at a desired time, for example, only when the pump is to be activated for operation. When the pump operation is concluded, the projection can be retracted and the valve body 14 can return to its idle position. For example, the projection that can be pulled out or retracted can be also designed as a bolt or bar.

Supplementary, the valve actuator 51 can be used as a positioning aid for the pump module 1 and as an aid to guarantee that the pump module 1 is correctly inserted in the receptacle.

The wobble pump base module 40 comprises a recess 52 into which the second flexible wall section 20 of the valve unit 12 of the pump module 1 can escape when the valve body 14 transfers to operation position. In this embodiment, the recess 52 is arranged in the cover 44 (see FIGS. 30 to 32). In this way, it is possible to design the pump module 1 as a flat and small component.

Furthermore, the wobble pump base module 40 comprises a pressure sensor 66 (see FIG. 32). The pressure sensor 66 is designed in such a way that it determines a value by means of the deformation of the flexible wall section 11 of the pressure measuring chamber 10, which value reflects the pressure inside the pressure measuring chamber 10. Such pressure sensors 66 are well-known to experts. In this embodiment, the pressure sensor 66 is arranged in the housing of the wobble pump base module 40.

Alternatively or additionally, the pressure sensor 66 or a further pressure sensor can be in contact with the membrane 4 of the pump module 1, to measure the pressure in the pump channel 5, as described above.

In addition, the wobble pump base module 40 comprises a pretensioning device 56 (for example, see FIG. 33). The pretensioning device 56 is designed in such a way that the wobble device 41 is flexibly pretensioned against a pump module 1 received in the receptacle 42.

Because of the fact that the wobble device 41 is resiliently pretensioned against the pump module 1, it is possible to achieve a defined position between the wobble device 41 and the pump module 1, and/or the pump module 1 exerts sufficient contact pressure on the membrane 4 of the pump module 1. In this way, it can also be guaranteed that the properties of the pump do not change, or change only minimally when the pump module is exchanged. It is possible also to compensate axial tolerances.

In this embodiment, the wobble device 41 is pretensioned in axial direction by the pretensioning device 56. Accordingly, the wobble device 41 is movably mounted in axial direction (shown in FIG. 33 by the axis). The pretensioning device 56 presses the wobble device 41 up to a limit stop 83 into a starting position in which the wobble device 41 extends into the receptacle when the pump module 1 is not inserted in the receptacle 42. The axis 67 has a vertical position in relation to the bottom part of the receptacle 42. As a result, the bar 56 of the wobble device 41 extends into the receptacle 42. When the pump module 1 is inserted, the bar 56 comes in contact with the membrane 4 of the pump module 1 and seals the membrane 4 at a compression point. When the pump module 1 is completely inserted, the wobble device 41 is pressed against pretension through the pump module 1 in the direction of the housing.

In this embodiment, the pretensioning device 56 comprises several springs 69 which pretension the wobble pump drive system 43 together with the wobble device 41. To guarantee that the wobble device 41 does not tilt toward the receptacle 42 or tilts only slightly, the wobble pump drive system 43 with which the wobble device 41 is connected is mounted on several guide pins 70. The pretensioning device 56 is rigidly connected with the housing of the wobble pump base module 40, here the bottom of the housing 64. According to a further embodiment (not shown), the pretensioning device is integrated in the cover 44 of the pump base module 40. The pretensioning device is designed in such a way that is exerts pressure on the pump module 1 when the pump module 1 is inserted in the receptacle 42 and the cover 44 is closed. As a result, the pump module 1 is pressed against the wobble device. Consequently, the pump module 1 is pretensioned when the cover 44 is closed.

Moreover, an axial pretension of the wobble device 41 along the axis 67 makes it possible that during the pump operation the wobble device 41 can perform an overlapping movement in axial direction in addition to oscillation. The same applies when the pump module 1 is pretensioned axially against the wobble device 41. For specific models of the pump module 1 and wobble device 41, this allows for a secure, periodically circulating compression of the pump channel 5 and especially for a secure simultaneous closure of pump channel inlet 6 and pump channel outlet 7. Furthermore, the wobble device 41 comprises a positioning aid 57. The positioning aid 57 is designed in such a way that it centers the wobble device 41 on the extension of the motor shaft. A corresponding receptacle or recess of the pump module 1 allows for an axial movement of the wobble device 41. In this embodiment, the wobble device 41 comprises a central, dome-shaped projection. The pump module 1 comprises a corresponding sigmoidal depression 22 into which the positioning aid engages when the pump module is inserted in the receptacle 42. Preferably, there is no direct contact between positioning aid 57 and pump module 1 to guarantee the flexibility of the wobble device and to avoid friction loss.

By means of the wobble pump drive system 43, the wobble device 41 is set in oscillation. FIGS. 33 to 36 show wobble pump base modules 40 with different embodiments of a wobble pump drive system 43.

The wobble pump drive system 43 comprises a motor 69, by means of which a drive shaft 70 can be set in rotation. The drive shaft 70 is turned about the axis 67. The rotation process is transformed into oscillation of the wobble device 41 by means of a transmission mechanism.

Preferably, the motor comprises an electric motor, for example a direct-current motor, a step motor or a piezomotor. Preferably, one or several batteries are used for energy supply for the motor (not shown), which are situated in the wobble pump base module 40. Alternatively or additionally, it is possible to use an external energy supply.

In a first embodiment (shown in FIG. 33), the wobble pump drive system 43 comprises a transmission element 71. By means of ball bearing 73, the transmission element 71 is swivel-mounted in a carrier in which also the motor 69 is situated. The transmission element 71 is rigidly connected with the drive shaft 70, so that it follows the rotary motion of the drive shaft 70.

The transmission element 71 comprises a lateral pin 74. In its axis, the pin 74 is inclined toward the axis 67. The inclination angle of the pin 74 corresponds to a 90-degree angle minus a tumbling angle 68. The tumbling angle 68 determines the inclination of the wobble device 41 toward the axis 67.

A ball bearing 75 is arranged on the pin 74. The outer edge of the ball bearing 75 rests on the edge of the rear side of the wobble device 41.

The wobble device 41 is kept in position by a center pin 77 which is swivel-mounted by means of ball bearings 76 inside the transmission element 71. At the same time, the center pin 77 engages loosely in a central recess 78 of the wobble device 41. The rotational axis of the center pin 77 corresponds to the axis 67. The ball bearing center pin 77 is not turning, which minimizes friction loss in the recess 78. Because of its shape, the recess 78 of the wobble device 41 makes it possible that the wobble device 41 sufficiently tilts toward the center pin 77. Alternatively, it is possible to rigidly connect the wobble device 41 with the center pin 77, wherein the wobble device 41 assumes the predetermined inclination toward the center pin 77.

The rotation of the drive shaft 70 results in rotation of the pin 77 about the rotational axis 67. The ball bearing 75 arranged on the pin 77 unrolls on the outer edge of the wobble device and sets in rotation the wobble device 41 as a result of the inclination of the pin 77.

The axis of symmetry of the wobble device 41 is inclined toward the rotational axis 67 by the tumbling angle 68. In this embodiment, it is advantageous that it is very easy to center the wobble device, which is here designed as a wobble plate.

In a variation of the embodiment (shown in FIG. 34), the wobble device 41 is swivel-mounted in the transmission element 71 by means of two ball bearings 78 which are centrically positioned about the axis of symmetry of the wobble device 41. The two ball bearings 78 uncouple the rotary motion of the transmission element 71 from the wobble device 41. In this embodiment, the alignment of the wobble device 41 is predetermined. In a different model of the embodiment (shown in FIG. 35), the transmission element comprises a pin 79 in addition to the first pin 74. The pin 79 is arranged collinear to the first pin 74 on the opposite side of the axis 67. A second ball bearing 75 is arranged on the second pin 79. The outer edge of the ball bearing 75 also rests on the edge of the wobble device 41. Through a rotation of the drive shaft 70, the two ball bearings 75 arranged on the pins 74, 79 unroll on opposite places of the outer edge of the wobble device 41, which sets the wobble device 41 in oscillation. Compared to the embodiment shown in FIG. 33, in this way, it is possible to stabilize oscillation.

In a further model of the embodiment (shown in FIG. 36), the inclined pin 74 of the transmission element 71 and the ball bearing is replaced by a magnet 80. The wobble device 41 comprises a ring-shaped magnet 81 which is arranged on the rear side of the wobble device facing the magnet 80. The magnet 80 of the transmission element 71 is restricted to a section of the angle. By turning the transmission element 71, the magnet 80 moves over the ring-shaped magnet 81 of the wobble device 41. The magnets 80, 81 are arranged with poles opposite to one another, so that the magnets 80, 81 touch each other. Because of the repelling effect of the magnets 80, 81, the wobble device 41 is set in oscillation by means of the rotation of the magnet 80 of the transmission element 71. In this embodiment, it is advantageous that friction loss is minimized. The wobble device is centered by means of the center pin 77.

In a further model (shown in FIG. 37), the wobble device 41 is designed in the form of a flat, semi-rigid and flexibly deformable wobble plate.

Because of the fact that the wobble device 41 is resilient, it is possible to guarantee that sufficient contact pressure is exerted on the membrane 4 of an inserted pump module 1 during the entire pump cycle.

In this case, the wobble device 41 is resiliently pretensioned by a pretensioning device 56. However, alternatively, it is possible to relinquish such a pretensioning device 56.

Furthermore, the wobble pump base module 40 comprises a flexible support plate 82. The support plate 82 is arranged in the receptacle 42, here at the bottom part of the receptacle 42. Tolerances existing between the pump module 1 inserted in the receptacle 42 and the cover 44 can be compensated through the flexibility of the support plate 82, wherein the cover 44 can have a rigid design. As a result, the pump module 1 is firmly pressed against the cover by the pretensioning device 56 and is positively positioned. The axial amplitude of the wobble device 41, produced by the pretensioning device 56, is greater than the maximum permissible axial flexibility of the pump module 1. As a result, it can be guaranteed that the membrane 4 is securely compressed.

Basically, it is possible to vary the number of ball bearings 73, 75, 76, 78 used in the embodiments. By using several ball bearings, it is possible to define or stabilize the movement more exactly. Reducing the number of ball bearing is advantageous from the aspect of having a compact and weight-saving structure.

Figure 38A:
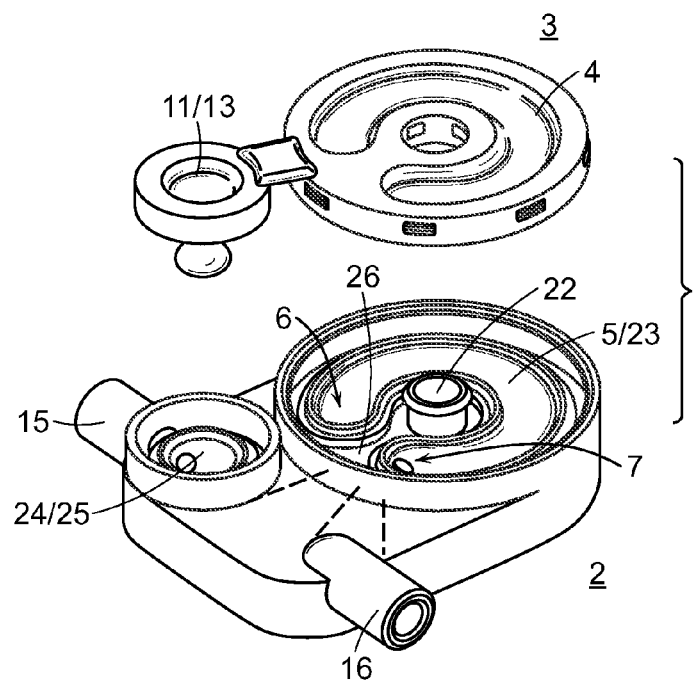
Figure 38B:
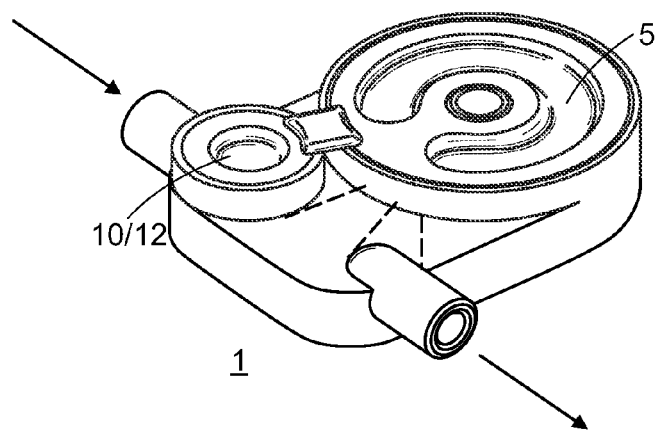
Figure 38C:
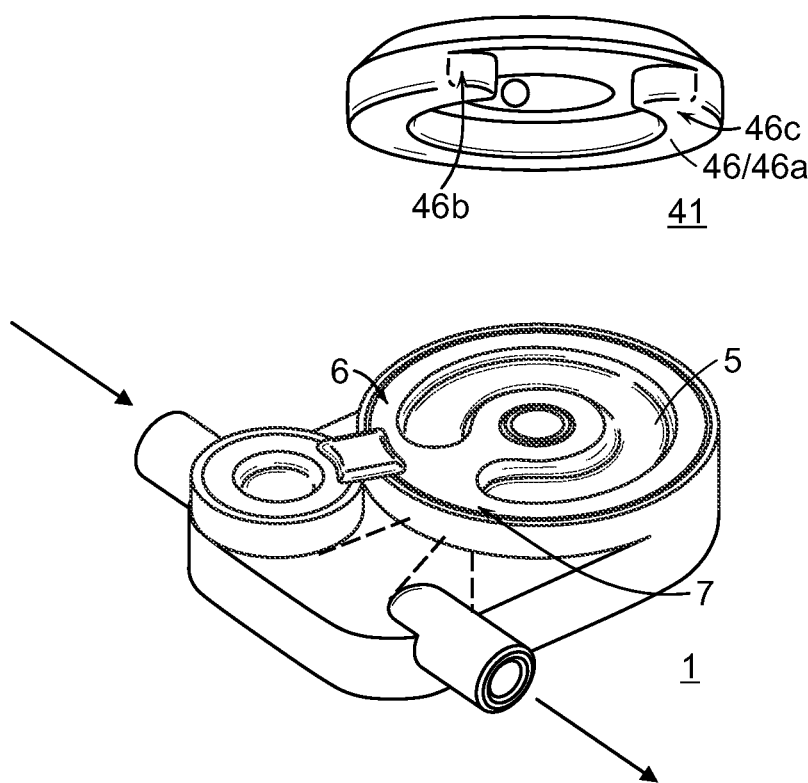

FIGS. 38.a to 38.c show a preferred embodiment of the pump module 1 in non-assembled and assembled state.

FIG. 38.a shows the base 2 with a ring-shaped recess or groove 23 which form together with the membrane 4 the pump channel 5. It also shows the first connector 15, the pump channel inlet 6, the pump channel outlet 7 and the second connector 16. A further recess 24 or 25 is arranged between the first connector 15 and the second connector 16, which recess is provided for receiving the flexible wall section. Dotted lines indicate the transitions from the pump channel inlet 6 and the pump channel outlet 7 to the first and second connector 15 or 16.

Furthermore, FIG. 38.a shows the cover 3 with the membrane 4 which form together with the recess 23 in the base 2 the ring-shaped pump channel 5. A bulge (not visible) is arranged on the surface of the membrane 4. Basically, the membrane or at least the surface of the membrane has a convex design, in particular, at least in sections. This design ensures that the wobble device 41 compresses the membrane 4 as even as possible. In addition, the cover 3 supports the flexible wall section 11 or 13, for example a membrane which forms or can form together with the further recess 24 or 25 a valve unit 12 or a pressure measuring chamber 10.

FIG. 38.b shows the disposable pump module 1 in assembled state. FIG. 38.c indicates the interaction with the wobble device 41 or the wobble plate 41. For the process of pumping, the bar of the wobble plate 41 engages in the ring-shaped pump channel 5 or presses from the top against the membrane 4 (not shown). In the area between the pump channel inlet 6 and the pump channel outlet 7, the bar 46 comprises an interruption to bridge the bar 26.

In one embodiment, the pump module 1 can be produced with lateral measurement smaller than 4 cm by 4 cm. The pump volume per rotation can range between 10 to 50, preferably 20 to 30 microliters. Currently, a pump volume of up to approximately 200 ml/h and/or a total pumpable volume of up to 25 L can be achieved by means of an invention-based wobble pump. In the previously examined pressure areas, the pump module 1 and/or the wobble pump base module 40, which receives the pump module 1, are quite sensitive toward pressure fluctuations at the pump channel inlet 6 and/or the pump channel outlet 7. For example, currently, with a variable backpressure at the pump channel outlet 7 of higher than 0 bar up to 1000 mbar, it is possible to achieve flow rates that have a deviation of lower than approximately 3%. With a variable pressure at the pump channel inlet 6 in a range of −100 mbar up to +100 mbar, it is possible to achieve flow rates that have a deviation of lower than approximately 5%. Because of the fact that the pump module 1 can be produced at low cost, it can preferably be provided as a disposable item.

As previously described and shown in exemplary manner in FIG. 3, it is possible to design the bar 46 of the wobble device 41 with a consistent height. The previous description also shows that the wobble device 41 can be designed with a bar 46 that has a varying height, preferably an increasing height. In this case, the edge of the bar 46 is not located in a mutual plane.

Figure 39A:
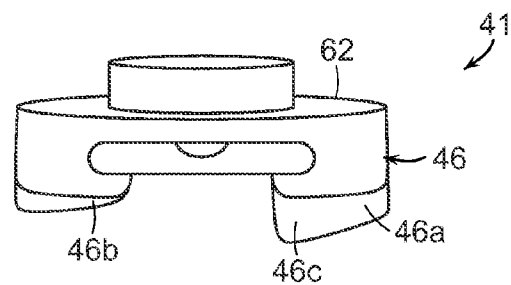
Figure 39B:
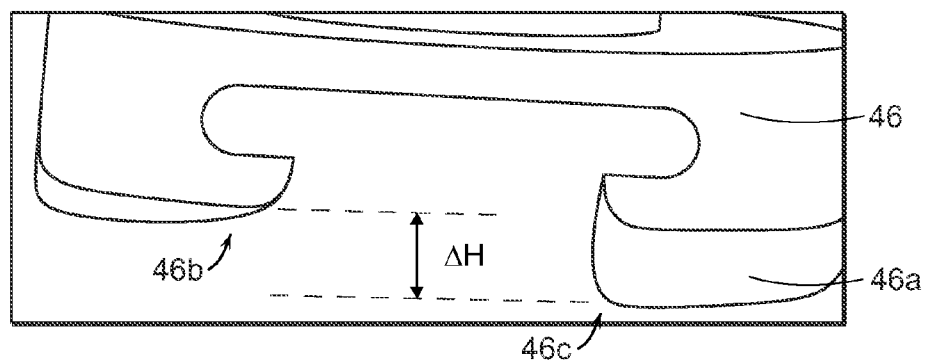

In a further embodiment of a wobble device 41 having a bar 46 with varying height, the bar 46 provides a type of ramp 46a. This is illustrated in FIGS. 39.a and 39.b. For this purpose, FIG. 39.b shows an enlarged representation of the bridging area of the wobble plate 41 shown in FIG. 39.a. For better visibility, the ramp 46a in both figures is not shown according to scale. The edge of the bar 46 associated with the pump module 1 is not located in a plane. Preferably, the height of the bar increases continuously. A ramp 46a is formed. At the same time, it is possible that the increase changes throughout the circumference of the wobble plate 41. For example, it can increase or decrease, or remain constant. The deep-set or long section 46c of the bar 46 (in relation to the base 62 of the wobble device 41) is associated with the pump channel outlet 7 of the pump module 1. The high-set or short section 46b of the bar 46 (in relation to the base 62 of the wobble device 41) is associated with the pump channel inlet 6 of the pump module 1 (see also FIG. 38.c). During oscillation, the wobble plate 41 is tilted downward when the interruption in the bar 46 runs along the bar 26 in the base. As a result, it is possible that during oscillation the wobble device 41 simultaneously securely closes or compresses the pump channel inlet 6 and pump channel outlet 7 of the pump module 1. As a result, it is especially possible to prevent or at least reduce backflow problems.

Because of the design of the ramp 46a, it is prevented that the pump channel outlet 7 is opened when the wobble plate 41 continues to oscillate, while the pump channel inlet 6 is still closed or no pressure has been built in the pump channel 5. The ramp 46a has the effect that the wobble plate is not abruptly lifted up when the wobble plate 41 continues to oscillate and the pump channel outlet 7 is not abruptly opened, which would result from low pressure in the pump channel 5, and thus a so-called "backflow" into the pump channel 5 by means of the pump channel outlet 7 would occur. The "backflow" represents an undesired inflow of fluid at the pump channel outlet 7.

The difference in height $\Delta H$ between the two sections 46b and 46c of the ramp 46a is indicated with a double arrow in FIG. 39.b. Preferably, the difference in height $\Delta H$ ranges from approximately 1/100 mm to approximately 1 mm, preferably from approximately 1/10 mm to approximately 3/10 mm. Consequently, the increase of the ramp 46a ranges from approximately 1/100 mm to approximately 1 mm, preferably from approximately 1/10 mm to approximately 3/10 mm, distributed across the circumference of the wobble plate 41, in particular across an angular range of approximately 300° to approximately 360°. The ramp 46a can be provided by a material removal on the bar 46 or the edge of the bar (shown in FIGS. 39.a and 39) and/or by a material deposit on the bar 46 or the edge of the bar. As an alternative or addition, the ramp 46a can also be provided by a material removal on the and/or by a material deposit on the membrane 4. As a further alternative or addition it is also possible to design the pump channel 5 of the pump module 1 with a ramp.

Figure 40A:
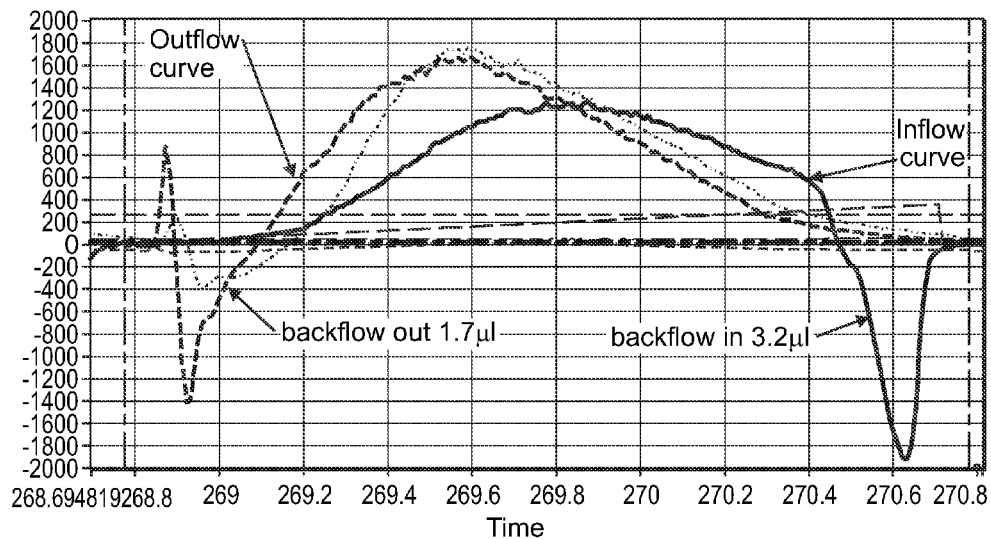
Figure 40B:
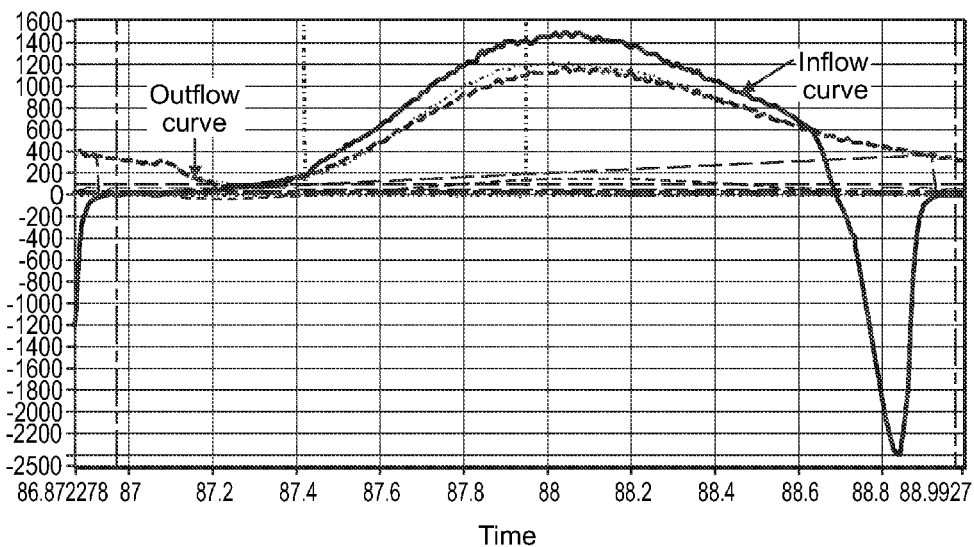

By means of the ramp 46a it is possible to prevent or at least reduce the backflow. In this regard, FIGS. 40.a and 40.b show calculations involving the pump performance with and without ramp 46a. In each case, the respective pump volume is shown as a function of time for a pump cycle. The two curves shown describe the pump performance at the pump channel inlet 6 ("inflow curve") and the pump channel outlet 7 ("outflow curve"). The positive values describe the volume pumped into the pump channel 5 ("inflow curve"), or the volume pumped out of the pump channel 5 ("outflow curve"). The negative values describe the volume pumped out of the pump channel 5 ("inflow curve") or the volume pumped into the pump channel 5 ("outflow curve"). In this case, especially the so-called "backflow out" is undesired, an undesired inflow or outflow of the fluid at the pump channel outlet 7. FIG. 40.a shows the pump performance without ramp 46a with a resulting "backflow out" of 1.7 microliters. FIG. 40.b shows the pump performance with ramp 46a with a resulting lower or basically repressed backflow.

Instead of a wobble device 41 having a bar and recess (shown in FIGS. 33 to 40), it is alternatively possible to use a wobble device 41 having a planar contact surface (shown in FIG. 9). Correspondingly, the pump module 1 is designed with a toric membrane 4.

The wobble pump base module 40 and the pump module 1 together form a wobble pump system for pumping a fluid. The pump module 1 and the wobble pump base module 40 are made compatible, especially the wobble device 41 of the wobble pump base module 40 with the pump channel 5 of the pump module 1 and the form of the pump module 1 with the form of the receptacle 42 of the wobble pump base module 40. Such a wobble pump system represents a pump with defined pump properties in which the components of the pump contaminated by a transported fluid can be quickly replaced in a simply manner by changing the pump module. The pump module 1 can be produced with compact structure in an inexpensive manner as a disposable item ("disposable"). Particularly for special applications, the pump module 1 can be integrated in a tube set or transfer system.

In addition, the pump module 1 can comprise a one-way valve which prevents an undesired backflow of the fluid to be transported. The one-way valve can be arranged in pump direction behind the pump channel outlet 7 or before the pump channel inlet 6. In particular, it is possible to provide at least two one-way valves which are arranged behind the pump channel outlet 7, as well as before the pump channel inlet 6. Preferably, a one-way valve is located between the first connector 15 and the pump channel inlet 6 and/or between the second connector 16 and the pump channel outlet 7. For example, the at least one one-way valve can be designed as a flexible membrane flap. Such membrane flaps are well-known to experts. Preferably, the one-way valve is formed by the base 2 and/or the cover 3 and a flexible membrane.

The invention-based pump module 1 can be produced in an inexpensive and robust manner. By designing the pump channel 23 at least from membrane 4 and base 2, it is possible to produce a pump channel 23 with defined and reproducible measurements. By means of a periodically circulating membrane deformation it is possible to achieve high accuracy in the production rate. Using the invention-based pump module 1 with a wobble device has the advantage that the mechanical stress of the membrane 4 because there is no rolling or sliding contact with the bodies deforming the membrane 4. is minimized Because of the fact that the pump module 1 can be produced in an inexpensive and reproducible manner, the invention-based pump module 1 qualifies as a disposable item ("disposable") intended merely for single use.

The embodiments of a pump module 1, a wobble pump base module 40 and an wobble pump system described above can especially be used in the medical field. These devices are especially preferred for use as enteral pumps, for example, for pumping nutrition solutions or for use as infusion pumps for intravenously infusing medications. It is also possible to use them for other applications.

The invention claimed is:

1. A wobble pump base module comprising a wobble pump drive system, a wobble device, a housing having a receptacle for receiving a pump module, and a pre-tensioning device, wherein the pre-tensioning device flexibly pre-tensions the pump module housed in the receptacle against the wobble device, the receptacle configured such that the pump module, without using additional tools, is manually inserted in the receptacle and is manually removed from the receptacle, and a cover configured to close the receptacle and a pump module received in the receptacle, wherein the pre-tensioning device is at least partially integrated in the cover so that the pump module is pre-tensioned when the cover is closed.

2. The wobble pump base module of claim 1, wherein the pre-tensioning device is configured to pre-tension the wobble device against a reception of the pump module.

3. The wobble pump base module of claim 2, wherein the wobble device is mounted to be axially movable along a rotational axis.

4. The wobble pump base module of claim 2, further comprising a cover configured to close the receptacle and a pump module received in the receptacle, wherein the pre-tensioning device is at least partially integrated in the cover so that the pump module is pre-tensioned when the cover is closed.

5. The wobble pump base module of claim 1, wherein the wobble device is mounted to be axially movable along a rotational axis.

6. The wobble pump base module of claim 5, further comprising a cover configured to close the receptacle and a pump module received in the receptacle, wherein the pre-tensioning device is at least partially integrated in the cover so that the pump module is pre-tensioned when the cover is closed.

7. The wobble pump base module of claim 1, wherein the receptacle is in the form of a depression formed with in a first surface of the housing.

8. The wobble pump base module of claim 7, wherein the receptacle is sized and shaped to conform to an outer shape of the pump module.

9. A wobble pump system comprising a pump module, and a wobble pump base module, the wobble pump base module including a wobble pump drive system, a wobble device, a housing having a receptacle for receiving the pump module, and a pre-tensioning device, wherein the pre-tensioning device flexibly pre-tensions the pump module housed in the receptacle against the wobble device; wherein the pump module includes a base and a flexibly deformable membrane, wherein the base and the flexibly deformable membrane form a line-shaped pump channel that is curved at least in sections in such a way that, through a wobbling deformation of the flexibly deformable membrane, a fluid is pumped through the line-shaped pump channel, wherein the pump module is received in the receptacle of the wobble pump base module in such a way that the pump module and the wobble device are resiliently pressed against each other through the re-tensioning device, the receptacle configured such that the pump module, without using additional tools, is manually inserted in the receptacle and is manually removed from the receptacle, and a cover configured to close the receptacle and the pump module received in the receptacle, wherein the pre-tensioning device is at least partially integrated in the cover so that the pump module is pre-tensioned when the cover is closed.

10. The system of claim 9, wherein the wobble device is mounted to be axially movable along a rotational axis.

11. The wobble pump system of claim 9, wherein the receptacle is in the form of a depression formed with in a first surface of the housing.

12. The wobble pump system of claim 11, wherein the receptacle is sized and shaped to conform to an outer shape of the pump module.

13. The wobble pump base module of claim 9, wherein the pre-tensioning device is configured to pre-tension the wobble device against a reception of the pump module.

14. The wobble pump base module of claim 9, wherein the wobble device is mounted to be axially movable along a rotational axis.

15. A wobble pump base module comprising a wobble pump drive system, a wobble device, a housing having a receptacle for receiving a pump module, and a pre-tensioning device, wherein the pre-tensioning device flexibly pre-tensions the pump module housed in the receptacle against the wobble device, the receptacle configured such that the pump module, without using additional tools, is manually inserted in the receptacle and is manually removed from the receptacle, wherein the receptacle is in the form of a depression formed with in a first surface of the housing and a cover configured to contact the first surface of the housing and the pump module.

16. The wobble pump base module of claim 15, wherein the pre-tensioning device is configured to pre-tension the wobble device against a reception of the pump module.

17. The system of claim 15, wherein the wobble device is mounted to be axially movable along a rotational axis.

18. A wobble pump system comprising a pump module, and a wobble pump base module, the wobble pump base module including a wobble pump drive system, a wobble device, a housing having a receptacle for receiving the pump module, and a pre-tensioning device, wherein the pre-tensioning device flexibly pre-tensions the pump module housed in the receptacle against the wobble device; wherein the pump module includes a base and a flexibly deformable membrane, wherein the base and the flexibly deformable membrane form a line-shaped pump channel that is curved at least in sections in such a way that, through a wobbling deformation of the flexibly deformable membrane, a fluid is pumped through the line-shaped pump channel, wherein the pump module is received in the receptacle of the wobble pump base module in such a way that the pump module and the wobble device are resiliently pressed against each other through the re-tensioning device the receptacle configured such that the pump module, without using additional tools, is manually inserted in the receptacle and is manually removed from the receptacle, wherein the receptacle is in the form of a depression formed with in a first surface of the housing, and a cover configured to contact the first surface of the housing and the pump module.

* * * * *